(12) United States Patent
Conboy et al.

(10) Patent No.: US 9,163,215 B2
(45) Date of Patent: Oct. 20, 2015

(54) GENERATION OF LINEAGE-RESTRICTED PROGENITOR CELLS FROM DIFFERENTIATED CELLS

(71) Applicant: The Regents of the University of California, Oakland, CA (US)

(72) Inventors: Irina M. Conboy, El Sobrante, CA (US); Preeti Paliwal, Albany, CA (US)

(73) Assignee: The Regents of the University of California, Oakland, CA (US)

(*) Notice: Subject to any disclaimer, the term of this patent is extended or adjusted under 35 U.S.C. 154(b) by 58 days.

(21) Appl. No.: 13/653,021

(22) Filed: Oct. 16, 2012

(65) Prior Publication Data

US 2013/0129687 A1    May 23, 2013

Related U.S. Application Data

(60) Provisional application No. 61/548,638, filed on Oct. 18, 2011.

(51) Int. Cl.
| | |
|---|---|
| C12N 5/00 | (2006.01) |
| C12N 5/077 | (2010.01) |
| A61K 35/34 | (2015.01) |
| C12Q 1/02 | (2006.01) |
| C12Q 1/68 | (2006.01) |
| G01N 33/50 | (2006.01) |

(52) U.S. Cl.
CPC ............ *C12N 5/0652* (2013.01); *A61K 35/34* (2013.01); *C12N 5/0658* (2013.01); *C12Q 1/025* (2013.01); *C12Q 1/6897* (2013.01); *G01N 33/5061* (2013.01); *C12N 2501/73* (2013.01); *C12N 2506/1323* (2013.01)

(58) Field of Classification Search
None
See application file for complete search history.

(56) References Cited

U.S. PATENT DOCUMENTS

| | | | |
|---|---|---|---|
| 6,326,201 | B1 | 12/2001 | Fung et al. |
| 7,692,012 | B2 | 4/2010 | Woscholski et al. |
| 2009/0258423 | A1 | 10/2009 | Dugas et al. |

OTHER PUBLICATIONS

Chasteen, Structure and Bonding 53: 105-138 (1983).*
Vasconsuelo et al., J. Endocrinol. 196: 385-397 (2008).*
Song et al., Apoptosis 13: 383-393 (2008).*
Mu et al., PLoS ONE 6(2): e16699 (Feb. 2011).*
Pathak et al., J. Immunol. 167: 3391-3397 (2001).*
Brezak et al., Cancer Res. 64: 3320-3325 (2004).*
Ait-Si-Ali et al., "A Suv39h-dependent mechanism for silencing S-phase genes in differentiating but not in cycling cells", EMBO J 23:605-615 (2004).
Bennett and Tonks, "Regulation of Distinct Stages of Skeletal Muscle Differentiation by Mitogen-Activated Protein Kinases," Science 278(5341):1288-1291 (1997).
Bunz et al., "Requirement for p53 and p21 to Sustain G2 Arrest After DNA Damage," Science 282(5393):1497-1501 (1998).
Burns et al., "Diabetes Mellitus: A Potential Target for Stem Cell Therapy," Current Stem Cell Research & Therapy 1 (2):255-266 (2006).

(Continued)

*Primary Examiner* — Patricia A Leith
*Assistant Examiner* — Erin M Bowers
(74) *Attorney, Agent, or Firm* — Edward J. Baba; Shweta Chandra; Bozicevic, Field & Francis LLP

(57) ABSTRACT

Method for reprogramming differentiated cells into lineage restricted progenitor cells is provided. The method may include contacting differentiated cells with inhibitors of tyrosine phosphatases and apoptosis to de-differentiate differentiated cells into lineage restricted progenitor cells.

15 Claims, 32 Drawing Sheets

(56) References Cited

OTHER PUBLICATIONS

Caretti et al., "The Polycomb Ezh2 methyltransferase regulates muscle gene expression and skeletal muscle differentiation," Genes & Dev 18:2627-2638 (2004).
Carnac et al., "The retinoblastoma-like protein p130 is involved in the determination of reserve cells in differentiating myoblasts," Curr Biol 10(9):543-546 (2000).
Castaldi et al., "Bisperoxovanadium, a phospho-tyrosine phosphatase inhibitor, reprograms myogenic cells to acquire a pluripotent, circulating phenotype," FASEB J 21(13):3573-3583 (2007).
Cayrol et al., "p21 binding to PCNA causes G1 and G2 cell cycle arrest in p53-deficient cells," Oncogene 16 (3):311-320 (1998).
Chen et al., "The coactivator-associated arginine methyltransferase is necessary for muscle differentiation: CARM1 coactivates myocyte enhancer factor-2," J Biol Chem 277(6):4324-4333 (2002).
Conboy and Conboy, "Preparation of adult muscle fiber-associated stem/precursor cells," Methods Mol Biol 621:149-163 (2010).
de la Serna et al., "Mammalian SWI/SNF complexes promote MyoD-mediated muscle differentiation," Nature Genetics 27(2):187-190 (2001).
Delgado et al., "Dynamic gene expression during the onset of myoblast differentiation in vitro," Genomics 82 (2):109-121 (2003).
Duckmanton et al., "A Single-Cell Analysis of Myogenic Dedifferentiation Induced by Small Molecules," Chem Biol 12 (10):1117-1126 (2005).
Dugas et al., "Functional Genomic Analysis of Oligodendrocyte Differentiation," J Neurosci 26(43):10967-10983 (2006).
Endo and Nadal-Ginard, "Reversal of myogenic terminal differentiation by SV40 large T antigen results in mitosis and apoptosis," J Cell Sci 111:1081-1093 (1998).
Endo and Nadal-Ginard, "Transcriptional and posttranscriptional control of c-myc during myogenesis: its mRNA remains inducible in differentiated cells and does not suppress the differentiated phenotype," Mol Cell Biol 6 (5):1412-1421 (1986).
Forcales and Puri, "Signaling to the chromatin during skeletal myogenesis: Novel targets for pharmacological modulation of gene expression," Semin Cell Dev Biol 16(4-5):596-611 (2005).
Friday and Pavlath, "A calcineurin- and NFAT-dependent pathway regulates Myf5 gene expression in skeletal muscle reserve cells," J Cell Sci 114:303-310 (2001).
Gusconi and Puri, "Chromatin: the interface between extrinsic cues and the epigenetic regulation of muscle regeneration," Trends Cell Biol 19(6):286-294 (2009).
Hjiantoniou et al., "Twist induces reversal of myotube formation," Differentiation 76(2):182-192 (2008).
Hochedlinger et al., "Ectopic Expression of Oct-4 Blocks Progenitor-Cell Differentiation and Causes Dysplasia in Epithelial Tissues," Cell 121(3):465-477 (2005).
Kim et al., "Direct reprogramming of human neural stem cells by OCT4," Nature 461(1):649-654 (2009).
Lassar et al., "Regulatory mechanisms that coordinate skeletal muscle differentiation and cell cycle withdrawal," Curr Opin Cell Biol 6(6):788-794 (1994).
Latella et al, "Long-term fate of terminally differentiated skeletal muscle cells following E1A-initiated cell cycle reactivation," Cell Death and Differentiation 7:145-154 (2000).
Latella et al., "Reconstitution of Cyclin D1-Associated Kinase Activity Drives Terminally Differentiated Cells into the Cell Cycle," Mol Cell Biol 21(16):5631-5643 (2001).
Li et al., "The Ink4/Arf locus is a barrier for iPS cell reprogramming," Nature 460:1136-1139 (2009).
Loof et al., "Plasticity of Mammalian Myotubes Upon Stimulation with a Thrombin-activated Serum Factor," Cell Cycle 6(9):1096-1101 (2007).
McGann et al., "Mammalian myotube dedifferentiation induced by newt regeneration extract," Proc Natl Acad Sci USA 98(24):13699-13704 (2001).
McKinsey et al., "Signaling chromatin to make muscle," Curr Opin Cell Biol 14(6):763-772 (2002).
Siow and Pearson, "Vascular Smooth Muscle Cells: Isolation, Culture, and Characterization," Methods in Molecular Medicine 46:237-245 (2001).
Mitcheson et al., "Cultured adult cardiac myocytes—Future applications, culture methods, morphological and electrophysiological properties," Cardiovascular Research 39(2):280-300 (1998).
Nouspikel and Hanawalt, "DNA repair in terminally differentiated cells," DNA Repair 1(1):59-75 (2002).
Odelberg et al., "Dedifferentiation of Mammalian Myotubes Induced by msx1," Cell 103(7):1099-1109 (2000).
Okazaki and Holtzer, "Myogenesis: fusion, myosin synthesis, and the mitotic cycle," Proc Natl Acad Sci USA 56 (5):1484-1490 (1966).
Olson, "Interplay between proliferation and differentiation within the myogenic lineage," Dev Biol 154(2):261-272 (1992).
Pajalunga et al., "DNA Replication Is Intrinsically Hindered in Terminally Differentiated Myotubes," PLoS ONE 5(7): e11559 (2010).
Pajcini et al., "Transient Inactivation of Rb and ARF Yields Regenerative Cells from Postmitotic Mammalian Muscle," Cell Stem Cell 7(2):198-213 (2010).
Palacios and Puri, "The epigenetic network regulating muscle development and regeneration," J Cell Physiol 207 (1):1-11 (2006).
Palacios et al., "TNF/p38α/Polycomb Signaling to Pax7 Locus in Satellite Cells Links Inflammation to the Epigenetic Control of Muscle Regeneration," Cell Stem Cell 7(4):455-469 (2010).
Rosania et al., "Myoseverin, a microtubule-binding molecule with novel cellular effects," Nat Biotechnol 18:304-308 (2000).
Rosenblatt et al., "Culturing satellite cells from living single muscle fiber explants," In Vitro Cell Dev. Biol Anim 31 (10)173-779 (1995).
Rudnicki and Jaenisch, "The MyoD family of transcription factors and skeletal myogenesis," Bioessays 17(3):203-209 (1995).
Sartorelli and Caret, "Mechanisms underlying the transcriptional regulation of skeletal myogenesis," Curr Opin Genet Dev 15(5):528-535 (2005).
Tiainen et al., "Terminally differentiated skeletal myotubes are not confined to G0 but can enter G1 upon growth factor stimulation," Cell Growth Differ 7(8):1039-1050 (1996).
Utikal et al., "Immortalization eliminates a roadblock during cellular reprogramming into iPS cells," Nature 460:1145-1148 (2009).
Weintraub, "The MyoD family and myogenesis: redundancy, networks, and thresholds," Cell 75(7):1241-1244 (1993).
Yoshida et al., "Cell heterogeneity upon myogenic differentiation: down-regulation of MyoD and Myf-5 generates 'reserve cells'," J Cell Sci 111:769-779 (1998).

\* cited by examiner

Figure 8        Supplementary Table S1 related to Figure 7

Title: Chromatin enzymes gene expression PCR array of inhibitor mix treated and untreated Cre-Lox YFP myotubes
Fold change compared with untreated samples, data normalized to internal control Hprt1 ; n=3

DNA Methyltransferases

| Gene Table | | fold change | p value |
|---|---|---|---|
| DNA methyltransferase (cytosine-5) 1 | Dnmt1 | 0.2802 | 0.000101 |
| DNA methyltransferase 3A | Dnmt3a | 0.6556 | 0.004961 |
| DNA methyltransferase 3B | Dnmt3b | 0.5286 | 0.080713 |

Histone Methyltransferases

| | | fold change | p value |
|---|---|---|---|
| Euchromatic histone methyltransferase | Ehmt1 | 0.5877 | 0.009607 |
| Euchromatic histone lysine N-methyltrar | Ehmt2 | 0.3483 | 0.000995 |
| DOT1-like, histone H3 methyltransferase | Dot1l | 1.009 | 0.86116 |
| Coactivator-associated arginine methylt | Carm1 | 0.3299 | 0.000005 |
| Myeloid/lymphoid or mixed-lineage leul | Mll3 | 0.8128 | 0.034003 |
| Protein arginine N-methyltransferase 1 | Prmt1 | 0.2685 | 0.000004 |
| Protein arginine N-methyltransferase 2 | Prmt2 | 0.6487 | 0.017779 |
| Protein arginine N-methyltransferase 3 | Prmt3 | 0.2933 | 0.00001 |
| Protein arginine N-methyltransferase 5 | Prmt5 | 0.4931 | 0.00514 |
| Protein arginine N-methyltransferase 6 | Prmt6 | 0.2539 | 0.00007 |
| Protein arginine N-methyltransferase 7 | Prmt7 | 0.2509 | 0.000111 |
| Protein arginine N-methyltransferase 8 | Prmt8 | 0.8377 | 0.35693 |
| SET domain, bifurcated 2 | Setdb2 | 0.2754 | 0.000107 |
| SET and MYND domain containing 1 | Smyd1 | 0.4755 | 0.000245 |
| SET and MYND domain containing 3 | Smyd3 | 0.39 | 0.016298 |
| Suppressor of variegation 3-9 homolog 1 | Suv39h1 | 0.2572 | 0.000274 |

SET Domain Proteins (Histone Methyltransferase Activity)

| | | fold change | p value |
|---|---|---|---|
| SET domain containing 1A | Setd1a | 0.6199 | 0.02114 |
| SET domain containing 1B | Setd1b | 0.3221 | 0.000021 |

Figure 8 (cont)

| | | fold change | p value |
|---|---|---|---|
| SET domain containing 2 | Setd2 | 0.5405 | 0.000948 |
| SET domain containing 3 | Setd3 | 0.5549 | 0.001781 |
| SET domain containing 4 | Setd4 | 0.619 | 0.04822 |
| SET domain containing 5 | Setd5 | 0.7751 | 0.002836 |
| SET domain containing 6 | Setd6 | 0.3739 | 0.000873 |
| SET domain containing (lysine methyltra | Setd7 | 0.9867 | 0.798832 |
| SET domain containing (lysine methyltra | Setd8 | 0.3482 | 0.00002 |
| SET domain, bifurcated 1 | Setdb1 | 0.4354 | 0.002307 |
| Nuclear receptor-binding SET-domain pr | Nsd1 | 0.1796 | 0.001767 |
| Ash1 (absent, small, or homeotic)-like (D | Ash1l | 0.7027 | 0.000163 |
| Myeloid/lymphoid or mixed-lineage leuk | Mll5 | 0.817 | 0.03376 |
| | Suv420h1 | | |
| Suppressor of variegation 4-20 homolog | | 0.959 | 0.707355 |
| Wolf-Hirschhorn syndrome candidate 1 | Whsc1 | 0.6508 | 0.208791 |

DNA / Histone Demethylases

| | | fold change | p value |
|---|---|---|---|
| Lysine (K)-specific demethylase 1 | Kdm1 | 0.5753 | 0.002929 |
| Lysine (K)-specific demethylase 5B | Kdm5b | 1.3056 | 0.002714 |
| Lysine (K)-specific demethylase 5C | Kdm5c | 1.0505 | 0.509009 |
| Lysine (K)-specific demethylase 4A | Kdm4a | 0.6965 | 0.074036 |
| Lysine (K)-specific demethylase 4C | Kdm4c | 0.5481 | 0.003366 |
| KDM1 lysine (K)-specific demethylase 6E | Kdm6b | 0.8613 | 0.322889 |

Histone Acetyltransferase

| | | fold change | p value |
|---|---|---|---|
| Activating transcription factor 2 | Atf2 | 0.4992 | 0.001086 |
| Chromodomain protein, Y chromosome | Cdyl | 0.3822 | 0.003219 |
| Class II transactivator | Ciita | 0.4651 | 0.003666 |
| Cysteine and glycine-rich protein 2 bindi | Csrp2bp | 0.44 | 0.001079 |
| Establishment of cohesion 1 homolog 1 | Esco1 | 0.5529 | 0.004866 |
| Establishment of cohesion 1 homolog 2 | Esco2 | 0.0201 | 0.000277 |
| Histone aminotransferase 1 | Hat1 | 0.3455 | 0.003945 |
| K(lysine) acetyltransferase 2A | Kat2a | 0.4552 | 0.001466 |

Figure 8 (cont)

| | | fold change | p value |
|---|---|---|---|
| K(lysine) acetyltransferase 2B | Kat2b | 0.5314 | 0.004812 |
| K(lysine) acetyltransferase 5 | Kat5 | 0.5563 | 0.000025 |
| MYST histone acetyltransferase 1 | Myst1 | 0.6555 | 0.000572 |
| MYST histone acetyltransferase 2 | Myst2 | 0.5368 | 0.00947 |
| MYST histone acetyltransferase (monoc | Myst3 | 0.5944 | 0.001797 |
| MYST histone acetyltransferase monocy | Myst4 | 1.071 | 0.089454 |
| Nuclear receptor coactivator 1 | Ncoa1 | 0.4379 | 0.000025 |
| Nuclear receptor coactivator 3 | Ncoa3 | 0.8058 | 0.04824 |
| Nuclear receptor coactivator 6 | Ncoa6 | 0.5692 | 0.000312 |

Histone Deacetylases

| | | fold change | p value |
|---|---|---|---|
| Histone deacetylase 1 | Hdac1 | 0.2986 | 0.001169 |
| Histone deacetylase 10 | Hdac10 | 0.3988 | 0.000134 |
| Histone deacetylase 11 | Hdac11 | 0.4246 | 0.002029 |
| Histone deacetylase 2 | Hdac2 | 0.4849 | 0.003515 |
| Histone deacetylase 3 | Hdac3 | 0.3566 | 0.000002 |
| Histone deacetylase 4 | Hdac4 | 0.574 | 0.005389 |
| Histone deacetylase 5 | Hdac5 | 0.905 | 0.395169 |
| Histone deacetylase 6 | Hdac6 | 0.4465 | 0.002219 |
| Histone deacetylase 7 | Hdac7 | 0.2385 | 0.000454 |
| Histone deacetylase 8 | Hdac8 | 0.3496 | 0.000011 |
| Histone deacetylase 9 | Hdac9 | 2.4922 | 0.000098 |

Histone Phosphorylation

| | | fold change | p value |
|---|---|---|---|
| Aurora kinase A | Aurka | 0.0936 | 0.000734 |
| Aurora kinase B | Aurkb | 0.0298 | 0.000149 |
| Aurora kinase C | Aurkc | 1.1626 | 0.407005 |
| NIMA (never in mitosis gene a)-related | Nek6 | 0.4443 | 0.001453 |
| P21 (CDKN1A)-activated kinase 1 | Pak1 | 0.5096 | 0.008357 |
| Ribosomal protein S6 kinase polypeptid | Rps6ka3 | 0.47 | 0.000185 |
| Ribosomal protein S6 kinase, polypeptid | Rps6ka5 | 0.5225 | 0.00328 |

Figure 8 (cont)

Histone Ubiquitination

| Description | Gene | fold change | p value |
|---|---|---|---|
| Ring finger protein 2 | Rnf2 | 0.5446 | 0.000601 |
| Ring finger protein 20 | Rnf20 | 0.4612 | 0.003659 |
| Myb-like, SWIRM and MPN domains 1 | Mysm1 | 0.5762 | 0.001501 |
| Ubiquitin-conjugating enzyme E2A, RAD | Ube2a | 0.5108 | 0.000178 |
| Ubiquitin-conjugating enzyme E2B, RAD | Ube2b | 0.5948 | 0.000032 |
| Ubiquitin specific peptidase 16 | Usp16 | 0.5124 | 0.000140 |
| Ubiquitin specific peptidase 21 | Usp21 | 0.3349 | 0.003446 |
| Ubiquitin specific peptidase 22 | Usp22 | 0.9347 | 0.635343 |
| DAZ interacting protein 3, zinc finger | Dzip3 | 0.3378 | 0.000205 |

Figure 9    Supplementary Table S2 related to Figure 7

Title: Epigenetic chromatin remodeling factors gene expression PCR array of 48 hours inhibitor mix treated and untreated Cre-Lox YFP+ myotubes
fold change as compared to untreated Cre-Lox YFP myotubes; data normalized to internal control Hprt1; n=3

| Gene Table | Gene | SWI/SNF Complex Components | |
|---|---|---|---|
| | | fold change | p value |
| AT rich interactive domain 1A (SWI-like) | Arid1a | 0.5139 | 0.000941 |
| AT rich interactive domain 2 (ARID, RFX-like) | Arid2 | 1.1292 | 0.61024 |
| INO80 homolog (S. cerevisiae) | Ino80 | 0.5237 | 0.091786 |
| SWI/SNF related, matrix associated, actin dependent reg | Smarca2 | 0.405 | 0.004372 |
| SWI/SNF related, matrix associated, actin dependent reg | Smarca4 | 0.4896 | 0.010709 |
| SWI/SNF related, matrix associated, actin dependent reg | Smarca5 | 0.4437 | 0.000304 |

| | | Polycomb Group Genes | |
|---|---|---|---|
| | | fold change | p value |
| Additional sex combs like 1 (Drosophila) | Asxl1 | 0.2215 | 0.005481 |
| Bmi1 polycomb ring finger oncogene | Bmi1 | 0.5094 | 0.014536 |
| C-terminal binding protein 1 | Ctbp1 | 0.4119 | 0.006344 |
| C-terminal binding protein 2 | Ctbp2 | 0.6145 | 0.03176 |
| Embryonic ectoderm development | Eed | 0.808 | 0.025648 |
| Enhancer of zeste homolog 2 (Drosophila) | Ezh2 | 0.2926 | 0.001839 |
| Polycomb group ring finger 1 | Pcgf1 | 0.4418 | 0.000222 |
| Polycomb group ring finger 2 | Pcgf2 | 0.3726 | 0.002136 |
| Polycomb group ring finger 3 | Pcgf3 | 0.378 | 0.001008 |
| Polycomb group ring finger 5 | Pcgf5 | 1.1002 | 0.457515 |
| Polycomb group ring finger 6 | Pcgf6 | 0.4073 | 0.001987 |
| Polyhomeotic-like 1 (Drosophila) | Phc1 | 0.3183 | 0.000213 |
| Polyhomeotic-like 2 (Drosophila) | Phc2 | 0.3491 | 0.005614 |
| Ring finger protein 1 | Ring1 | 0.2932 | 0.002136 |
| Ring finger protein 2 | Rnf2 | 0.4566 | 0.002243 |
| Suppressor of zeste 12 homolog (Drosophila) | Suz12 | 0.5097 | 0.005068 |
| Tripartite motif-containing 27 | Trim27 | 0.3284 | 0.000256 |

Figure 9 (cont)

Chromobox / Heterochromatin Protein 1 (HP1) Homologs

| | | fold change | p value |
|---|---|---|---|
| Chromobox homolog 1 (Drosophila HP1 beta) | Cbx1 | 1.5141 | 0.019283 |
| Chromobox homolog 2 (Drosophila Pc class) | Cbx2 | 0.5424 | 0.065306 |
| Chromobox homolog 3 (Drosophila HP1 gamma) | Cbx3 | 0.4285 | 0.000018 |
| Chromobox homolog 4 (Drosophila Pc class) | Cbx4 | 1.4252 | 0.165812 |
| Chromobox homolog 5 (Drosophila HP1a) | Cbx5 | 0.4326 | 0.010719 |
| Chromobox homolog 6 | Cbx6 | 0.3371 | 0.027217 |
| Chromobox homolog 7 | Cbx7 | 0.5283 | 0.066382 |
| Chromobox homolog 8 (Drosophila Pc class) | Cbx8 | 0.5651 | 0.053278 |

Bromodomain Proteins

| | | fold change | p value |
|---|---|---|---|
| Bromodomain adjacent to zinc finger domain 1A | Baz1a | 0.4418 | 0.000666 |
| Bromodomain adjacent to zinc finger domain, 1B | Baz1b | 0.4445 | 0.009715 |
| Bromodomain adjacent to zinc finger domain, 2A | Baz2a | 0.5529 | 0.014352 |
| Bromodomain adjacent to zinc finger domain, 2B | Baz2b | 0.6594 | 0.010662 |
| Bromodomain PHD finger transcription factor | Bptf | 0.6026 | 0.010645 |
| Bromodomain containing 1 | Brd1 | 0.7929 | 0.166437 |
| Bromodomain containing 2 | Brd2 | 0.8378 | 0.400538 |
| Bromodomain containing 3 | Brd3 | 0.2987 | 0.000091 |
| Bromodomain containing 4 | Brd4 | 0.5612 | 0.021213 |
| Bromodomain containing 7 | Brd7 | 0.3288 | 0.000914 |
| Bromodomain containing 8 | Brd8 | 0.4686 | 0.015597 |
| Bromodomain, testis-specific | Brdt | 0.45 | 0.032894 |
| Bromodomain and PHD finger containing, 1 | Brpf1 | 0.5864 | 0.015101 |
| Bromodomain and PHD finger containing, 3 | Brpf3 | 0.4847 | 0.047747 |
| Bromodomain and WD repeat domain containing 1 | Brwd1 | 0.4857 | 0.003992 |
| Bromodomain and WD repeat domain containing 2 | Brwd2 | 0.4948 | 0.150689 |
| Bromodomain and WD repeat domain containing 3 | Brwd3 | 0.6931 | 0.105762 |
| Protein kinase C binding protein 1 | Prkcbp1 | 0.394 | 0.000542 |

Methyl-CpG DNA Binding Domain (MDB) Proteins

Figure 9 (cont)

| | | fold change | p value |
|---|---|---|---|
| Methyl-CpG binding domain protein 1 | Mbd1 | 0.4415 | 0.013011 |
| Methyl-CpG binding domain protein 4 | Mbd4 | 0.3228 | 0.098793 |
| Methyl CpG binding protein 2 | Mecp2 | 0.5622 | 0.005048 |
| Histone H4 transcription factor | Hinfp | 0.5955 | 0.014102 |

Nucleosome-Remodeling and Histone Deacetylase (NuRD) Complex Components

| | | fold change | p value |
|---|---|---|---|
| Methyl-CpG binding domain protein 3 | Mbd3 | 0.467 | 0.000228 |
| Metastasis associated 1 | Mta1 | 0.2256 | 0.00095 |
| Metastasis-associated gene family, member 2 | Mta2 | 0.4076 | 0.006021 |
| Ngfi-A binding protein 2 | Nab2 | 0.3506 | 0.012904 |
| SPEN homolog, transcriptional regulator (Drosophila) | Spen | 0.5361 | 0.010526 |

Chromodomain / Helicase / DNA-Binding Domain (CHD) Proteins

| | | fold change | p value |
|---|---|---|---|
| Chromodomain protein, Y chromosome-like | Cdyl | 0.3479 | 0.014159 |
| Chromodomain protein, Y chromosome-like 2 | Cdyl2 | 0.3701 | 0.001201 |
| Chromodomain helicase DNA binding protein 1 | Chd1 | 0.643 | 0.027565 |
| Chromodomain helicase DNA binding protein 2 | Chd2 | 0.7769 | 0.299882 |
| Chromodomain helicase DNA binding protein 3 | Chd3 | 0.2065 | 0.00311 |
| Chromodomain helicase DNA binding protein 4 | Chd4 | 0.2697 | 0.000209 |
| Chromodomain helicase DNA binding protein 5 | Chd5 | 0.9573 | 0.907152 |
| Chromodomain helicase DNA binding protein 6 | Chd6 | 0.4302 | 0.02152 |
| Chromodomain helicase DNA binding protein 7 | Chd7 | 0.583 | 0.220002 |
| Chromodomain helicase DNA binding protein 8 | Chd8 | 0.348 | 0.00197 |
| Chromodomain helicase DNA binding protein 9 | Chd9 | 0.4845 | 0.00348 |

CCCTC-Binding Factor (Zinc Finger Protein)

| | | fold change | p value |
|---|---|---|---|
| CCCTC-binding factor | Ctcf | 0.3986 | 0.011822 |

Inhibitor of Growth (ING) Family Members

Figure 9 (cont)

|  |  | fold change | p value |
|---|---|---|---|
| Inhibitor of growth family, member 1 | Ing1 | 0.7074 | 0.008388 |
| Inhibitor of growth family, member 2 | Ing2 | 0.849 | 0.171073 |
| Inhibitor of growth family, member 3 | Ing3 | 0.5072 | 0.007244 |
| Inhibitor of growth family, member 4 | Ing4 | 0.359 | 0.000504 |
| Inhibitor of growth family, member 5 | Ing5 | 0.2221 | 0.000071 |

Plant Homeodomain (PHD) Proteins

|  |  | fold change | p value |
|---|---|---|---|
| Nuclear receptor-binding SET-domain protein 1 | Nsd1 | 0.1621 | 0.000805 |
| PHD finger protein 1 | Phf1 | 0.5498 | 0.104173 |
| PHD finger protein 13 | Phf13 | 0.455 | 0.019338 |
| PHD finger protein 2 | Phf2 | 0.3859 | 0.012938 |
| PHD finger protein 21B | Phf21b | 1.2346 | 0.20129 |
| PHD finger protein 3 | Phf3 | 0.5184 | 0.000765 |
| PHD finger protein 5A | Phf5a | 0.9231 | 0.655236 |
| PHD finger protein 6 | Phf6 | 0.2866 | 0.000026 |
| PHD finger protein 7 | Phf7 | 0.6561 | 0.019887 |

SEQUENCE LISTING

```
<160> NUMBER OF SEQ ID NOS: 16

<210> SEQ ID NO 1
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 1
gggaagccca tcaccatct                                                    19

<210> SEQ ID NO 2
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 2
gcctcacccc atttgatgtt                                                   20

<210> SEQ ID NO 3
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 3
gaccctacag acgcccacaa                                                   20
```

-continued

```
<210> SEQ ID NO 4
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 4
ccgtgatgct gtccacgat                                                   19

<210> SEQ ID NO 5
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 5
cggctctctc tgctcctttg                                                  20

<210> SEQ ID NO 6
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 6
gagtcgaaac acgggtcatc a                                                21

<210> SEQ ID NO 7
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 7
ccctcagtga gttcgattag c                                                21

<210> SEQ ID NO 8
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 8
ccttcctcgt cgtcctcttt c                                                21

<210> SEQ ID NO 9
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 9
gaacatctca gggccgaaaa                                                  20

<210> SEQ ID NO 10
<211> LENGTH: 22
<212> TYPE: DNA
<213> ORGANISM: Artificial sequence
```

```
<220> FEATURE:
<223> OTHER INFORMATION: Synthetic nucleic acid

<400> SEQUENCE: 10
tgcgcttgga gtgatagaaa tc                                          22

<210> SEQ ID NO 11
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 11
agaggacgtg tatgccatga                                             20

<210> SEQ ID NO 12
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 12
tggccatgtc ctcaatcttg t                                           21

<210> SEQ ID NO 13
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 13
gccgggtcag aaaaaatgg                                              19

<210> SEQ ID NO 14
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 14
agggcgcgag ttgatagct                                              19

<210> SEQ ID NO 15
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 15
gcacgacttc ttcaagtccg ccatgcc                                     27

<210> SEQ ID NO 16
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 16
gcggatcttg aagttcacct tgatgcc                                     27
```

GENERATION OF LINEAGE-RESTRICTED PROGENITOR CELLS FROM DIFFERENTIATED CELLS

GOVERNMENT RIGHTS

This invention was made with government support under federal grant no. AG027252 awarded by the National Institutes of Health. The government has certain rights in this invention.

FIELD OF THE INVENTION

The subject invention is directed to methods for generating lineage restricted progenitor cells. Aspects of the method include generating new cells in a subject in need thereof, using the lineage restricted progenitor cells. In addition, reagents, devices and kits thereof that find use in practicing the subject methods are provided.

INTRODUCTION

Maintenance and repair of tissue is essential for survival of multicellular organisms. However, there is a decline in maintenance and repair of tissue with aging and in certain diseases. In addition, mammals have a limited ability to regenerate damaged tissue or replace dead cells in a tissue as majority of cells in the tissue are in a differentiated state with limited proliferative capacity.

Skeletal muscle represents a classic example of terminal differentiation wherein myogenic proliferating cells expressing Pax7 and MyoD permanently withdraw from the cell cycle upon serum deprivation and physiologically fuse into multinucleated myotubes expressing muscle differentiation markers myogenin and eMyHC (Okazaki and Holtzer, Proc Natl Acad Sci USA 56, 1484-1490, 1966; Olson, Dev Biol 154, 261-272, 1992; Rudnicki and Jaenisch, Bioessays 17, 203-209, 1995). The regenerative capacity of muscle stem cells declines upon aging and in certain pathologies exemplified by Duchenne muscular dystrophy. Hence studying reprogramming of terminally differentiated muscle cells to their proliferating progenitors holds not only theoretical value but is also therapeutically relevant. The reprogramming from myotubes to myogenic precursor cells is particularly challenging since myogenic proliferating cells not only undergo post-mitotic arrest, but also physically fuse with each other to form multinucleated myotubes during their terminal differentiation. Once these cells terminally differentiate, they are incapable of re-entering into mitosis even when switched to serum rich medium (Endo and Nadal-Ginard, Mol Cell Biol 6, 1412-1421, 1986; J Cell Sci 111 (Pt 8), 1081-1093, 1998). In contrast, reserve cells (myoblasts which remain mononucleated upon serum withdrawal) can re-enter cell cycle when switched back to the mitogen-high serum rich growth medium (Carnac et al., Curr Biol 10, 543-546, 2000; Friday and Pavlath, J Cell Sci 114, 303-310, 2001; Yoshida et al., J Cell Sci 111 (Pt 6), 769-779, 1998). Over-expression of cyclin D1 and CDK4/6 or knocking down cell cycle inhibitors alone or in combination is insufficient for myotubes to enter mitosis (Latella et al., Mol Cell Biol 21, 5631-5643, 2001; Tiainen et al., Cell Growth Differ 7, 1039-1050, 1996). Studies in C2C12 cells have shown that a fraction of myotubes derived from this cell line can de-differentiate in the presence of newt extract, myoseverin, or when msxl or twist are over-expressed (Duckmanton et al., Chem Biol 12, 1117-1126, 2005; Hjiantoniou et al., Differentiation 76, 182-192, 2008; McGann et al., Proc Natl Acad Sci USA 98, 13699-13704, 2001; Odelberg et al., Cell 103, 1099-1109, 2000; Rosania et al., Nat Biotechnol 18, 304-308, 2000). However, the rare de-differentiated cells were not tested for their ability to contribute to muscle regeneration in vivo. Earlier work has also reported that C2C12 myotubes responsive to thrombin activated serum response factor triggers expression of immediate early genes but is not sufficient for S phase entry (Loof et al., Cell Cycle 6, 1096-1101, 2007). Interestingly, the same group also demonstrated that H3K9 di-methylation remains unperturbed in C2C12 myotubes in the presence of serum as opposed to salamander myotubes which readily enter cell proliferation. A recent study has shown deletion in Ink4a locus in C2C12 immortalized cell lines which provides an advantage to C2C12 cells to enter cell cycle upon knockdown of Rb. Knockdown of pRb in conjunction with Arf can induce cell cycle entry in primary myocytes but not in primary myotubes where nuclei get arrested at the onset of mitosis (Pajcini et al., Cell Stem Cell 7, 198-213, 2010). Nevertheless, the process of de-differentiation of primary multi-nucleated myotubes is still not well understood and most of the previous studies relied on the over-expression of exogenous genes. Some of the previous studies have employed single myocyte and myotube isolation and that can lead to preferential selection of those myotubes that survive such process and does not clear ambiguity of reserve cells which can come along with myotubes. Sparse plating of myoblasts was also tried, but that prevents formation of multinucleated myotubes and limits the study to myocytes.

As such, there is a need for methods and reagents for generating lineage restricted progenitor cells that may be used to provide differentiated cells.

SUMMARY

Method for reprogramming differentiated cells into lineage restricted progenitor cells is provided. The method may include contacting differentiated cells with inhibitors of tyrosine phosphatases and apoptosis to de-differentiate differentiated cells into lineage restricted progenitor cells.

The subject methods find use in generating muscle tissue in vitro and generating new muscle tissue in a subject in need thereof. In addition, reagents and kits thereof that find use in practicing the subject methods are provided.

In certain embodiments, the method for generating lineage-restricted progenitor cells from a differentiated cell, may include contacting a differentiated cell with an effective amount of an agent that inhibits tyrosine phosphatases and an effective amount of an agent that inhibits apoptosis under conditions sufficient for generation of lineage-restricted progenitor cells from the differentiated cell, wherein the differentiated cell and the lineage-restricted progenitor cells have the same lineage.

The differentiated cell used in the methods disclosed herein may be any differentiated cell, such as, those described in the present disclosure. In certain embodiments, the differentiated cell may be a myocyte and the lineage-restricted progenitor cells may be myogenic progenitor cells. In certain aspects of the invention, the myocyte may be a myocyte selected from the group consisting of a cardiomyoctyte, a smooth muscle myocyte, and a skeletal myocyte.

The agent that inhibits tyrosine phosphatases may be a small molecule. The agent that inhibits apoptosis may be a small molecule.

In some embodiments, the differentiated cell may be from a subject with a disease condition.

In certain cases, the contacting may be carried out ex vivo or in vivo.

The method may further include transferring the lineage-restricted progenitor cells to conditions that promote differentiation into differentiated cells of the same lineage as that of the differentiated cell contacted in the contacting step.

In certain cases, the transferring may include transferring the lineage-restricted progenitor cells into a subject. The subject may be in need of tissue regeneration.

In certain instances, the subject may be suffering from loss of muscle function and/or loss of muscle mass, and wherein the differentiated cell is a myocyte and the lineage-restricted progenitor cells are myogenic progenitor cells.

Also provided is a method of screening for an agent that inhibits tyrosine phosphatases and an agent that inhibits apoptosis and mediates generation of lineage-restricted progenitor cells from a differentiated cell. The method may include contacting a differentiated cell with a candidate agent that inhibits tyrosine phosphatases and a candidate agent that inhibits apoptosis under conditions sufficient for generation of lineage-restricted progenitor cells from the differentiated cell, wherein the differentiated cell and the have the same lineage; and determining whether lineage-restricted progenitor cells are produced, wherein the presence of lineage-restricted progenitor cells indicates that the candidate agent that inhibits tyrosine phosphatases and the candidate agent that inhibits apoptosis mediate generation of lineage-restricted progenitor cells from a differentiated cell. The differentiated cell may be a myocyte and the lineage-restricted progenitor cells may be myogenic progenitor cells.

A kit for use in generation of lineage-restricted progenitor cells from a differentiated cell is also disclosed. The kit may include an agent that inhibits tyrosine phosphatases and an agent that inhibits apoptosis. In certain cases, the agent that inhibits tyrosine phosphatases and the agent that inhibits apoptosis are small molecules.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1A. Schematic of the system. Wild type myoblasts (MB) derived from C57BL/6 mice were infected with Ad-Cre and subsequently co-cultured with Lox-YFP MB obtained from Rosa 26-YFP reporter mice in differentiation medium (DM) to form myotubes. The fusion of these two populations of MB led to the excision of stuffer sequence (excised floxed sequence) by Cre recombinase activity to give rise to lineage marked YFP expressing myotubes (shaded). Self fusion among the two populations of MB will give rise to YFP negative myotubes (colorless). These lineage marked myotubes were then used in de-differentiation studies. FIG. 1B. Fusion-dependent, Cre-Lox mediated labeling of myotubes upon co-culture of Ad-Cre MB with Lox-YFP MB in DM. As described in FIG. 1A, wild type MB were co-cultured with Lox-YFP MB (1:2 ratio) in DM to induce formation of myotubes. Endogenous YFP fluorescence in myotubes was observed by 72-96 hours as shown by epifluorescent images. In control infection with control Ad-RFP virus, no YFP fluorescence was observed. No YFP expression was observed upon co-culture of Ad-Cre MB and Lox YFP MB in GM where myoblasts did not undergo physiological fusion to form myotubes. FIG. 1C. Western blotting to determine YFP expression using lysates from Lox-YFP MB, Ad-Cre MB co-cultured with Lox-YFP MB in GM and parallel in DM. YFP protein was observed in the myotubes which arose from fusion of Ad-Cre and Lox-YFP MB in DM. FIG. 1D. qRT-PCR analysis for YFP gene expression. RNA was extracted from Ad-Cre and Lox-YFP MB co-cultured in GM and in DM for 96 hours to detect the levels of YFP and Cre recombinase by qRT-PCR. Data was normalized to internal control GAPDH. Error bars indicate mean and standard deviation, n=3. YFP mRNA levels was only observed in Ad-Cre-Lox-YFP$^+$ myotubes while Cre recombinase expressed in both the co-cultures of Ad-Cre and Lox-YFP MB in GM and in DM. The fusion-dependent marking of myotubes was clearly and robustly mediated by this adaptation of the Cre-Lox method, and no mononucleated cells expressed YFP.

FIG. 2A-D. YFP$^+$ myotubes obtained after Cre-Lox fusion express muscle differentiation marker and do not incorporate BrdU. Cre-Lox YFP$^+$ myotubes cultures were co-immunostained with muscle differentiation markers eMyHC (FIG. 2A), myogenin (FIG. 2B), p21 (FIG. 2C), and DNA synthesis label BrdU (FIG. 2D) along with anti-YFP antibody. Representative images are shown.

FIG. 3A. Myotube de-differentiation strategy. MB infected with Ad-Cre were co-cultured with Lox-YFP MB in DM for 4 days to give rise to YFP$^+$ myotubes. These were treated with 10 µM BpV+10 uM Q-VD in parallel with other experimental conditions for two days in DM. The treated myotubes were then switched to myoblast GM which was replaced fresh every day. YFP$^+$ mononucleated cells were observed around day 10. De-differentiation of YFP$^+$ myotubes to YFP$^+$ proliferative cells. FIG. 3B. YFP$^+$ myotubes cultures were treated with the BpV+Q-VD and photographed every day. The addition of BpV+Q-VD led to morphological changes and when switched to GM these cells expanded as YFP$^+$ mononucleated cells in 72 hours (white arrow shows YFP$^+$ mononucleated cells). Representative high magnification images of de-differentiation experiment over the course of 10 days with live Hoechst is shown by epifluorescent microscopy. FIG. 3C. No-treatment (Untreated: UT): Untreated YFP$^+$ myotubes were grown in similar conditions and did not show any de-differentiation events. These data demonstrate that inhibitor mix is necessary and sufficient for de-differentiation of genetically labeled myotubes into expanding mononucleated cells. FIG. 3D. Reprogrammed YFP$^+$ mononucleated cells rapidly divide. Cre-Lox-YFP$^+$ myotubes reprogrammed as depicted in FIGS. 3B and 3C, were pulsed with BrdU for 24 hours and co-stained with anti YFP and BrdU antibodies. Arrows indicate representative BrdU$^+$YFP$^+$ cells in treated conditions. Untreated cultures of YFP$^+$ myotubes do not show any YFP$^+$ mononucleated cells though BrdU incorporation is seen in non YFP cycling mononucleated cells. Inset shows magnified images. FIG. 3E. Quantification of percent of BrdU$^+$/YFP$^+$ mononucleated cells out of total number of YFP$^+$ myotubes (shown are the mean and standard deviations, n=3 p<0.05). Note that many reserve myoblasts re-entered cell cycle and incorporated BrdU in GM (both in the presence of BpV+Q-VD and in control untreated cultures); these cells, however, were reliably distinguished in our experiments by the absence of YFP.

FIG. 4A. Co-immunostaining of FACS-sorted, proliferating YFP$^+$ mononucleated cells for (i) Pax7 and (ii) MyoD along with anti-YFP antibody was performed and representative images are shown. FIG. 4B. Histogram quantifies Pax7 and MyoD expressing YFP$^+$ mononucleated cells which represents mean and standard deviation of three independent experiments. FIG. 4C. De-differentiated, FACS sorted, YFP$^+$ cells were expanded in GM and cultured in DM for 96 hours where myoblasts typically form myotubes; cultures were co-immunostained with antibodies specific to YFP and to myotube specific marker (i) eMyHC ii) myogenin, as well as (ii) the CDK inhibitor p21. FIG. 4D. Western blotting with antibodies specific for Pax7, MyoD, eMyHC, p21, myogenin and YFP was performed using protein extracts from Cre-Lox-YFP myotubes, de-differentiated YFP$^+$ mononucleated cells and re-differentiated YFP+ cells as indicated. Actin served as loading control. FIG. 4E. Gene expression analysis of muscle differentiation markers. qRT-PCR data in log scale for Pax7, MyoD, myogenin, p21 and eMyHC depicts the relative gene expression of re-differentiated myotubes to de-differentiated YFP$^+$ cells. These data represent the mean and standard error for three independent experiments.

FIGS. 6A and 6B. 4 day old Ad-Cre-Lox-YFP myotubes were untreated/treated with inhibitor mix for 48 hours, followed by immuno-detection of myogenin (a), p21 (b) and YFP (green), using antibodies specific for these proteins. Myogenin and p21 were down-regulated in a subset of YFP$^+$ myotubes (shown by white arrows). Control myotubes did not change expression of muscle differentiation markers. FIGS. 6C and 6D. The histogram quantifies the percent of YFP$^+$/myogenin$^+$, YFP$^+$/myogenin$^-$ cells and YFP$^+$/p21+ and YFP$^+$/p21$^-$ in the experiment shown in FIGS. 6A and 6B (n=3±S.D.; p*<0.001, p<0.05). FIGS. 6E and 6F. Ad-Cre-Lox-YFP myotubes untreated/treated with BpV+Q-VD for 48 hours were analyzed for protein and mRNA levels. Protein lysates were subjected to western blotting for antibodies against p21, myogenin and eMyHC. Actin served as a loading control. q-RT-PCR was performed on RNA lysates for gene expression of p21, p15, p16, myogenin and eMyHC. Data were normalized to GAPDH and represents mean and standard deviation of three independent experiments each done in triplicates (n=3±S.D.; p*<0.001, p<0.05). Untreated sample was taken as 1.

FIGS. 7A and 7B. Clustergram analysis of chromatin remodeling factors and enzymes for Ad-Cre-Lox YFP myotubes treated and untreated with BpV+Q-VD (inhibitor mix) for 48 hours using SA Biosciences/Qiagen PCR arrays. 0.5 ug RNA isolated from three independent set of experiments of Ad-Cre-Lox YFP myotubes were reverse transcribed and gene expression profile monitored. FIGS. 7C and 7D. Histogram representation for few set of genes normalized by Hprt gene levels. Control untreated was taken as 1. (n=3±S.D.; p*<0.001, p<0.05).

FIG. 8 shows Supplementary Table 51 that provides a complete list of chromatin factor and enzyme genes modulated by inhibitor mix treatment.

FIG. 9 shows Supplementary Table S2 that provides a complete list of chromatin factor and enzyme genes modulated by inhibitor mix treatment.

FIGS. 11A, 11C and 11D: In the presence of BpV alone, myotubes did show apoptosis and few of them gave rise to YFP+ mononucleated cells albeit at very low frequency (~1.18%) in comparison to inhibitor mix treatment which augmented the de-differentiation frequency to around ~12-13%. FIG. 11B: In control experiments, no YFP$^+$ mononucleated cells were observed in untreated YFP$^+$ myotubes in the presence of Q-VD alone.

FIG. 13A: Images that show ruling out any spurious YFP expression in the absence of Cre expressing cells and in the presence of inhibitor mix, 4 day old Lox YFP myotube cultures were treated with the inhibitor mix and then switched to growth medium. FIGS. 13B and 13C: Images that show no YFP$^+$ mononucleated cells were observed in the cultures in spite of altered morphology of myotubes.

DETAILED DESCRIPTION

Figure 1:
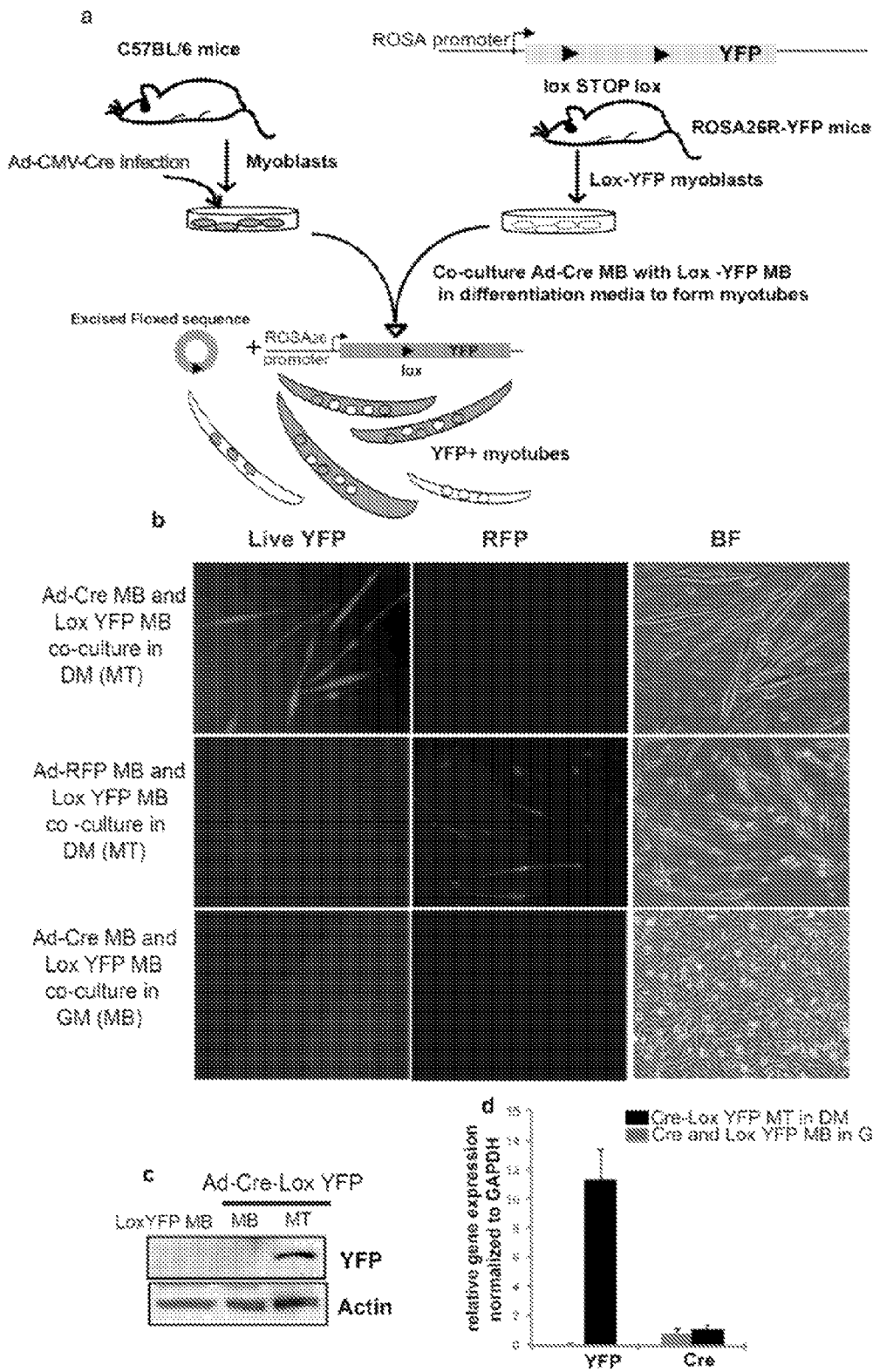
FIG. 1. Lineage marking of primary myotubes by Cre-Lox method.

Method for reprogramming differentiated cells into lineage restricted progenitor cells is provided. The method may include contacting differentiated cells with inhibitors of tyrosine phosphatases and apoptosis to de-differentiate differentiated cells into lineage restricted progenitor cells, where the differentiated cell and the lineage restricted progenitor cells have the same lineage.

Before the present methods, reagents and kits are described further, it is to be understood that this invention is not limited to particular methods, reagents and kits described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the muscle tissue" includes reference to one or more muscle tissues and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The phrase "differentiated cell" as used herein refers to a post-mitotic cell of a cell lineage that has differentiated into a mature, functional cell of a tissue. A differentiated cell expresses markers that are well-known to the artisan as characteristic of a mature cell fate. In addition, because differentiated cells are post-mitotic, they do not incorporate BrdU into their DNA or express markers that are typically expressed in proliferating cells, e.g. Ki67, PCNA, Anillin, AuroraB, Survivin, and the like. An example of a differentiated cell is a hepatocyte, a neuron, a myocyte, such as, a cardiomyocyte, a myofiber, and the like.

The term "dedifferentiation" or "dedifferentiates" as used herein refers to the process of reprogramming of a differentiated cell into a less differentiated state than the differentiated cell in the same cell lineage. In other words, when a differentiated cell dedifferentiates, the cell loses traits, e.g., morphology, expression of certain genes, functional capabilities, etc. of the differentiated cell and acquire traits of cells of the lineage that are less mature.

The phrase "lineage-restricted progenitor cells" as used herein refers to cells having a defined lineage and that divide to produce cells having the same lineage. In other words, a lineage-restricted progenitor cell has committed to a certain lineage and hence is not a pluripotent cell that can produce different cell types. Rather, a lineage-restricted progenitor cell divides to produce cells of the same lineage as the lineage-restricted progenitor cell. Lineage-restricted progenitor cells are identifiable by certain markers, such as, expression of one or more marker proteins that are known in the art to be characteristic of a progenitor cell for their cell lineage. In addition, progenitor cells are typically mitotic, and thus incorporate BrdU into their DNA and/or express one or more markers, e.g. proteins that are typically expressed in mitotic cells, e.g. Ki67, PCNA, Anillin, AuroraB, and Survivin. An example of lineage-restricted progenitor cell is a progenitor cell of the muscle lineage, i.e., a myogenic progenitor cell, namely a myoblast, as it can give rise to more myoblasts and/or post-mitotic muscle precursors that differentiate to produce myotubes.

The phrase "myogenic progenitor cells" as used herein refers to cells that divide to produce more myogenic progenitor cells that are capable of differentiating into post-mitotic muscle precursors and/or myotubes. A myogenic progenitor cell may be a myoblast. A myogenic progenitor cell is identifiable by a mononucleated morphology, and/or presence of proliferation marker, such as, Ki67, and/or BrdU incorporation, and/or expression of myogenic markers such as, MyoD1, Pax7, and the like.

The phrase "tyrosine phosphatase" as used herein refers to an enzyme that removes phosphate group from the tyrosine amino acid of a substrate, such as, a protein substrate. Tyrosine phosphatases include phosphatases that include the active site called the CX5R motif.

The term "proliferate" as used herein refers to division of cells by mitosis, i.e., cells undergoing mitosis.

The phrase "expanded population" as used herein refers to a population of cells that has proliferated, i.e., undergone mitosis, such that the expanded population has an increase in cell number, that is, a greater number of cells, than the population at the outset.

The term "explant" refers to a portion of an organ or tissue taken from the body of a subject and cultured in an artificial medium. Cells that are grown "ex vivo" are cells that are taken from the body in this manner, temporarily cultured in vitro, and returned to the body.

The term "primary culture" denotes a mixed cell population of cells from an organ or tissue. The word "primary" takes its usual meaning in the art of tissue culture.

The terms "individual," "subject," "host," and "patient," are used interchangeably herein and refer to any mammalian subject for whom diagnosis, treatment, or therapy is desired, particularly humans.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

An "isolated" cell is one which has been separated and/or recovered from a component of the environment in which it was produced. Contaminant components of its production environment are materials which would interfere with culturing, screening, diagnostic or therapeutic uses for the cell, and may include, other cell types, such as, neurons, proteins, enzymes, and other proteinaceous or nonproteinaceous components.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Method for Producing Lineage-Restricted Progenitor Cells

The methods of the present disclosure are based on the discovery that contacting a differentiated cell with an agent that inhibits tyrosine phosphatases and an agent that inhibits apoptosis results in dedifferentiation of the cell and production of progenitor cells that share the same lineage as the differentiated cell. The use of an agent that inhibits tyrosine phosphatases and an agent that inhibits apoptosis for contacting a differentiated cell provides for a synergistic effect that significantly increases the number of lineage restricted progenitor cells produced than that obtained by using either agent individually. Moreover, this synergistic effect is unexpected because either agent when used individually did not result in production of lineage restricted progenitor cells from a differentiated cell to a significant degree.

Accordingly, a method for generating lineage-restricted progenitor cells from a differentiated cell is provided. In certain embodiments, the method may include contacting a differentiated cell with an effective amount of an agent that inhibits tyrosine phosphatases and an effective amount of an agent that inhibits apoptosis under conditions sufficient for generation of lineage-restricted progenitor cells from the differentiated cell, wherein the differentiated cell and the lineage-restricted progenitor cells have the same lineage.

In certain cases, the contacting may result in division of the differentiated cell to produce progeny, which progeny may include lineage-restricted progenitor cells. In certain embodiments, dedifferentiation of the differentiated cell may precede division.

In some embodiments, subject differentiated cells are contacted with the agents ex vivo, that is, the differentiated cells are harvested from the body of a subject and contacted with the agents in vitro. In cases when the method is to be performed ex vivo, the differentiated cells may be cultured from an explant, e.g. biopsy or autopsy material, as a culture of primary cells. Methods of culturing differentiated cells from explants are typically specific for the type of primary cell being cultured, and are well known to one of ordinary skill in the art. For example, cardiomyocytes may be isolated and cultured as described in Mitcheson, J S et al. (1998) Cardiovascular Research 39(2):280-300. An exemplary method for isolation and culturing of human skeletal muscle myocytes is provided in Rosenblatt et al. (1995) In Vitro Cell Dev. Biol Anim 31(10):773-339 (for human skeletal muscle myocytes). An exemplary method for isolation and culturing of intestinal smooth muscle myocytes can be found in Graham M, and Willey A. (2003). Methods in Molecular Medicine Wound healing 78:417-423 Siow, RCM and Pearson, J D (2001) Methods in Molecular Medicine Angiogenesis protocols 46:237-245 provide methods for culturing of isolated vascular smooth muscle myocytes.

The differentiated cells are contacted ex vivo or in vivo with an effective amount of an agent that inhibits tyrosine phosphatases and an effective amount of an agent that inhibits apoptosis. As discussed herein, an agent that inhibits activity of tyrosine phosphatases is an agent that transiently antagonizes, inhibits or otherwise negatively regulates the activity of tyrosine phosphatases that are upregulated during maturation of a progenitor cell into a differentiated cell; agents that inhibit activity of tyrosine phosphatases can therefore act anywhere along a tyrosine phosphatase signaling pathway as it is known in the art. In certain embodiments, the inhibitor of tyrosine phosphatase activity acts directly on the tyosne phosphatases to inhibit its activity rather than a protein downstream to the tyrosine phosphatase in a signaling pathway. In certain cases, the agent may be an irreversible inhibitor of the tyrosine phosphatases. In other cases, the agent may be a transient or reversible inhibitor of the tyrosine phosphatases. Similarly, an agent that inhibits apoptosis is an agent that transiently or irreversibly antagonizes, inhibits or otherwise negatively regulates apoptosis. Agents that find use in the subject method of generating lineage-restricted progenitor cells from a differentiated cell are further described below.

An effective amount of an agent that inhibits tyrosine phosphatases is an amount that will reduce the overall activity of the tyrosine phosphatases or the downstream signaling pathway(s) in a differentiated cell by at least about 25%, at least 50%, at least 60%, at least 70%, at least 80%, at least 90%, at least 95%, by about 100%, such that the cell is able to enter mitosis and divide. Put another way, of the tyrosine phosphatases or the downstream signaling pathway(s) in a differentiated cell may be reduced by at least about 2-fold, usually by at least about 5-fold, e.g., 10-fold, 15-fold, 20-fold, 50-fold, 100-fold or more, as compared to a control, such as, a differentiated cell not contacted by the agent. For agents that inhibit the activity of tyrosine phosphatases ex vivo or in vitro, this effective amount may be measured by assaying dephosphorylation of substrates of the tyrosine phosphatases.

An effective amount of an agent that inhibits apoptosis is an amount that will reduce apoptosis in the differentiated cell or a dedifferentiated cell or a lineage restricted progenitor cell by at least about 25%, at least 50%, at least 60%, at least 70%, at least 80%, at least 90%, at least 95%, by about 100%, such that the differentiated cell is able to enter mitosis and divide to produce lineage-restricted progenitor cells. The effective amount of an inhibitor of apoptosis for use in vitro or ex vivo may be determined by assaying apoptosis in in the differentiated cell or a dedifferentiated cell or a lineage restricted progenitor cell. Apoptosis may be assayed as known in the art.

By transiently, it is meant that the inhibition is for a limited period of time, such as, for about 3 hours, about 6 hours, about 12 hours, about 1 day, about 2 days, about 3 days, about 5 days, about 7 days, about 10 days, about 15 days, about 20 days, or about 30 days.

The contacting of the differentiated cell with an effective amount of an agent that inhibits tyrosine phosphatases and an effective amount of an agent that inhibits apoptosis may be simultaneous or sequential. For example, the agent(s) that inhibits the activity of tyrosine phosphatases may be provided first, and the agent(s) that inhibits apoptosis may be provided second, or vice versa, e.g., 1 hour later, 3 hours later, 6 hours later, 12 hours later, 18 hours later, or 24 hours later, or even later.

In some embodiments, additional agents that promote mitosis may be provided to the cell at the contacting step, e.g. growth factors, e.g. bFGF, EGF, BMP, neuregulin, periostin; bovine groth serum or human growth serum, etc. In some embodiments, agents that promote cell cycle reentry are also provided to the cell in the contacting step. For example, in embodiments in which the subject differentiated cell is a skeletal muscle myocyte, agents that disrupt microtubules such a myoseverin peptide (Rosania G R et al. (2000) Nat. Biotechnol. 18(3):304-8) may be provided to fragment the multinucleated skeletal muscle cell. Such agents are typically used when the subject post-mitotic differentiated cell has a morphologically complex phenotype, for example, a cytoskeletal architecture that polarizes the cell, such as the architecture of a multinucleated muscle cell, neuron, hepatocyte, etc.

In some embodiments, the contacting step may be carried out in absence of growth factors, where the growth factors may be provided later, such as, 12 hours, 18 hours, 24 hours, 36 hours, 72 hours, or later after contacting the differentiated cell with an agents that inhibits tyrosine phosphatases and an agent that inhibits apoptosis. The agents may be removed after a certain period of time, i.e., the contacting step may be carried out for 1 hour, 1.5 hours, 2 hours, 3 hours, 4 hours, 6 hours, 8 hours, 12 hours, 18 hours, 24 hours, 36 hours, 72 hours, or longer. During the contacting step the culture medium may be replaced with fresh medium containing the agents.

In embodiments in which the differentiated cells are induced to become lineage-restricted progenitor cells and divide in vivo, i.e., in situ, agents may be administered locally, that is, directly to the target site in a subject, i.e., the tissue, such as, a muscle tissue where treatment is needed. The agents may be provided in any number of ways that are known in the art, e.g., as a liquid (e.g. in any suitable buffer (saline, PBS, DMEM, Iscove's media, etc.)), as a paste, in a matrix support, conjugated to a solid support (e.g. a bead, a filter such as a mesh filter, a membrane, a thread, etc.), etc. The conditions in the tissue are typically permissive of dedifferentiation and division of lineage-restricted progenitor cells, and no alteration of the basal conditions is required with the exception of providing the agents as described above.

Inhibition of tyrosine phosphatases and apoptosis will induce the differentiated cell to become lineage-restricted progenitor cell and divide to produce more lineage-restricted progenitor cells. The lineage-restricted progenitor cell may undergo mitosis for a limited amount of time, i.e., 12 hours, 1 day, 2 days, 3 days, 5 days, 7 days, 10 days, 15 days, or 20 days. Accordingly, the lineage-restricted progenitor cells produced by the methods of the present disclosure may undergo 1 round of mitosis, up to 2 rounds of mitosis, up to 3 rounds, up to 4 rounds, up to 5 rounds, up to 6 rounds, up to 10 rounds, up to 30 rounds, up to 40 rounds, up to 50 rounds, or up to 60 rounds mitosis. As such, the lineage-restricted progenitor cells produced by the subject methods are unlike tumorigenic cells, which undergo unregulated mitosis, i.e., continue to divide for an unlimited amount of time. The period of time in which the lineage-restricted progenitor cells are actively dividing is known as the induction period. During the induction period, a lineage-restricted progenitor cells that is induced to divide will give rise to a population, or cohort, of progeny that are lineage-restricted cells. In other words, a lineage-restricted progenitor cells may give rise to 2 or more cells, 4 or more cells, 8 or more cells, 16 or more cells, 32 or more cells, 64 or more cells, 100 or more cells, 1000 or more cells, or 10,000 or more cells. In some embodiments, at least about 1%, about 2%, about 5%, about 8%, more usually about 10%, about 15%, about 20%, or about 50% of contacted differentiated cells in a population may be induced to dedifferentiate and divide.

Following production of lineage-restricted progenitor cells, these cells may be subject to conditions that induce the cells to differentiate to produce differentiated cell of the same lineage as that of the lineage-restricted progenitor cells and the differentiated cell from which the lineage-restricted progenitor cells were produced. In other embodiments, the lineage-restricted progenitor cells may spontaneously differentiate into differentiated cells.

In certain embodiments, the transferring of the cells induced to divide ex vivo to condition that promote differentiation is effected by transplanting the progeny into the tissue of a subject. Cells may be transplanted by any of a number of standard methods in the art for delivering cells to tissue, e.g. injecting them as a suspension in a suitable buffer (saline, PBS, DMEM, Iscove's media, etc.), providing them on a solid support, e.g. a bead, a filter such as a mesh filter, a membrane, etc. In certain embodiments, the differentiation may be carried out by changing the culture medium to a medium that promotes the differentiation of cells of that lineage, as is known in the art.

In general, the subject methods achieve the dedifferentiation of a differentiated cell without the use of exogenous gene expression to modulate the expression of gene(s) involved in maintaining differentiated cell in a differentiated state or genes mediating reversal of a differentiated cell into a dedifferentiate state.

Differentiated Cell

A variety of differentiated cells may be used in the methods provided in the present disclosure. As noted above, a differentiated cell is a cell that has completed differentiation to become mature functional cell. Examples of differentiated cells include a myocyte in skeletal or heart muscle, an islet cell in pancreas, a hepatocyte in liver, a neuron in central nervous system, a neuron in peripheral nervous system, an osteocyte in bone, hematopoietic cell from blood, and the like. A differentiated cell can be identified as such by the expression of one or more proteins or RNAs, i.e. markers for the type of differentiated cell, as known in the art.

In some embodiments, the subject differentiated cells are myocytes, which express one or more of myogenin, myosin heavy chain (MHC), and creatine kinase. In certain embodiments, the myocytes are cardiomyocytes, which are rod shaped and cross-striated in culture and express one or more of proteins cardiac troponin, eHand transcription factor, and cardiac-specific myosins. In certain embodiments, the myocytes are smooth muscle myocytes, which express smooth muscle actin. In certain embodiments, the myocytes are skeletal muscle myocytes, which express one or more of skeletal muscle myosins, skeletal muscle troponin, myoD.

In certain embodiments, the differentiated cell may be a myocyte and the contacting may result is division of the myocyte into myogenic progenitor cells. In certain embodiments, the myocyte may be selected from the group consisting of cardiomyoctyte, a smooth muscle myocyte, and a skeletal myocyte.

A skeletal muscle myocyte may be identified by expression of RNA or proteins, such as, eMyHC, myogenin, p21, p15, and p16 expression and/or by cell morphology, such as, shape, presence of multiple nuclei in a single cell, and/or lack of cell proliferation.

In certain embodiments, the differentiated cell used in the methods provided in the present disclosure may be isolated from a subject or an individual, such as, a patient needing tissue regeneration. For example, the differentiated cell may be isolated from a tissue sample obtained from a subject. In certain examples, the tissue sample may be a biopsy sample, such as, a biopsy sample of a muscle of the subject. In certain embodiments, the muscle tissue may be removed from the heart, blood vessel, intestine, or a limb of the subject. The differentiated cell may be isolated from the biopsy sample by methods known in the art. An exemplary method for isolation of myocytes from muscle tissue is described in (Conboy and Conboy, Methods Mol Biol 621, 149-163, 2010).

Differentiated cells useful for producing lineage-restricted cells include any post-mitotic mature cell from any tissue comprising post-mitotic mature differentiated cells, e.g., muscle, nervous system, pancreas, liver, etc., e.g., a cardiomyocyte from an individual with a heart condition, a myocyte from an individual with muscular dystrophy, a neuron from an individual with Alzheimer's disease, Parkinson's Disease, ALS, and the like, as described above.

Inhibitors

As noted above, the method includes contacting a differentiated cell with an agent that inhibits tyrosine phosphatases and an agent that inhibits apoptosis.

In certain embodiments, the agent that inhibits tyrosine phosphatases and the agent that inhibits apoptosis may be is a small molecule that is cell permeable.

A small molecule compound may range in molecular weight from 50 daltons to 2500 daltons, such as, 100 daltons to 2000 daltons, or 200 daltons to 1000 daltons, such as 100 daltons, 300 daltons, 400 daltons, 500 daltons, 800 daltons, 1000 daltons, 1500 daltons, or 2500 daltons.

Naturally occurring or synthetic small molecules of interest include numerous chemical classes, such as organic molecules, e.g., small organic compounds having a molecular weight of more than 50 daltons and less than about 2,500 daltons. An agent used in the methods disclosed herein may include functional group(s) for structural interaction with proteins, particularly hydrogen bonding, and typically include at least an amine, carbonyl, hydroxyl or carboxyl group. The agents may include cyclical carbon or heterocyclic structures and/or aromatic or polyaromatic structures substituted with one or more of the above functional groups.

Small molecule inhibitors of tyrosine phosphatases and apoptosis can be provided directly to the medium in which the cells are being cultured, for example, as a solution in DMSO, water, or other solvent.

In certain embodiments, the agent that inhibits tyrosine phosphatases may include a small molecule inhibitor of activity of tyrosine phosphatases. In general, the agent inhibits the activity of two or more tyrosine phosphatases, such as, at least two, three, four, or more tyrosine phosphatases.

In certain cases an agent that inhibits tyrosine phosphatases may be a vandate small molecule, peroxovanadium (pV) small molecule, or a bisperoxovanadium (bpV), or derivatives thereof. In certain embodiments, an agent that inhibits tyrosine phosphatases may include one or more of potassium bisperoxo (bipyridine) oxovanadate (bpV(bipy), potassium bisperoxo(1,10-phenanthroline)oxovanadate (pV(phenanthroline) or bpV(phen)), potassium bisperoxo (piconlinate) oxovanadate (pV(pic)) and potassium bisperoxo(phenylbiguanide) oxovanadate (pV(biguan)). In certain embodiments, one or more of the vanadium compounds such as those described in U.S. Pat. No. 7,692,012 may be used as an agent to inhibit tyrosine phosphatases.

In certain cases, the agent that inhibits tyrosine phosphatases may be an agent that is an inhibitor of protein tyrosine phosphatases (PTPs), such as, Class I PTPs that include receptor tyrosine phosphatases, non-receptor type PTPs, dual-specific phosphatases, such as, MAPK phosphatases, slingshots, phosphatase and tensin homologs (PTENs); Class II PTPs that include low molecular weight phosphotyrosine phosphatase; Class III PTPs that include Cdc25 phosphatases; and Class IV PTPs that include pTyr-specific phosphatases.

In certain cases, an agent that inhibits apoptosis may include an agent that inhibits one or more proteins that mediate apoptosis. In some examples, the agent may include one or more agents that inhibit one or more of a caspase, a calpain, and/or Bcl-xL. In certain cases, the agent may inhibit the function of one or more caspases. In some embodiments, the inhibitor may inhibit one or more of the caspases, such as, caspase 1, caspase 2, caspase 3, caspase 8, caspase 9, caspase1 0, and/or caspase 12.

In certain cases, an apoptosis inhibitor may be an agent that forms an irreversible thioether bond between the aspartic acid derivative in the inhibitor and the active site cysteine of the caspase with the displacement or the 2,6-difluorophenoxy leaving group. In certain cases, an agent that inhibits apoptosis may include N-(2-Quinolyl)valyl-aspartyl-(2,6-difluorophenoxy)methyl ketone which is a cell permeable, irreversible pan-caspase inhibitor, especially active against caspases 1, 3, 8, and 9. The compound is also referred to as "Q-VD-oPh" or "OPH-109" or Q-VD-OPH. The compound has a quinoline derivative (Q), a dipeptide, valine (V, in standard single letter code) and aspartic acid (D, in standard single letter code), and a non toxic 2,6-difluorophenoxy methylketone (OPH) group.

In certain embodiments, one or more agents that inhibit apoptosis may be used in the methods disclosed herein.

In certain cases, an agent that inhibits apoptosis may be a broad spectrum caspase inhibitor such as Q-VD-OPH, Z-VAD-FMK (ZVAD-fmk) or BOC-D-FMK (Boc-D-fmk).

One or more agents that inhibit the activity of tyrosine phosphatases may be used. Likewise, one or more agents that inhibit the apoptosis may be used. The agents may be provided to the differentiated cells individually or as a single composition, that is, as a premixed composition, of agents. When provided individually, the agents may be added to the subject differentiated cells simultaneously or sequentially at different times.

In certain cases, the agent that inhibits tyrosine phosphatases may be a broad spectrum inhibitor, i.e., it may inhibit the activity of two or more tyrosine phosphatases involved in promoting and/or maintain differentiated state of a differentiated cell, such as, three, or four, or five, or more tyrosine phosphatases.

In Vivo Use of Lineage Restricted Progenitor Cells

The progeny of the dedifferentiated cell, i.e., lineage-restricted progenitor cells may be used for supplying differentiating or differentiated cells to a recipient for regenerating tissue. For example, in embodiments of the above methods in which the differentiated cells are myocytes, transplanting lineage-restricted cells generated the methods described above into muscle, or producing lineage-specific cells in situ in the muscle by in vivo methods described above results in the generation of new muscle cells in the patient. Muscle regeneration as used herein refers to the process by which new muscle fibers form from myogenic progenitor cells or muscle precursor cells. The lineage-restricted progenitor cells produced by the subject methods may be administered to a patient in a composition. The composition will usually confer an increase in the number of new fibers by at least 1%, more preferably by at least 20%, and most preferably by at least 50%. The growth of muscle may occur by the increase in the fiber size and/or by increasing the number of fibers. The growth of muscle may be measured by an increase in wet weight, an increase in protein content, an increase in the number of muscle fibers, an increase in muscle fiber diameter, etc. An increase in growth of a muscle fiber can be defined as an increase in the diameter where the diameter is defined as the minor axis of ellipsis of the cross section. Productive muscle regeneration may be also monitored by an increase in muscle strength and/or agility.

Tissue regeneration therapy that employs the lineage-restricted cells produced by the subject methods are useful for treating subjects suffering from a wide range of diseases or disorders. For example, in embodiments in which the postmitotic differentiated cells are myocytes, subjects suffering from muscular disorders, e.g., acute cardiac ischemia, injury due to surgery (e.g. tumor resection) or physical trauma (amputation/gunshot wound), or degenerative heart diseases such as ischemic cardiomyopathy, conduction disease, and congenital defects, etc. could especially benefit from regenerative tissue therapies that use the lineage-restricted cells of the subject method.

Other examples of muscle disorders that could be treated with the subject cells, such as, allogeneic cells, autologous cells, and/or genetically modified autologous cells, include muscular dystrophies such as Duchenne dystrophy and Becker muscular dystrophy.

Other particular examples of muscle disorders that could be treated with the subject cells, either allogeneic cells, autologous cells, and/or genetically modified autologous cells, include the non-dystrophic myopathies such as congenital and metabolic myopathies, including glycogen storage diseases and mitochondrial myopathies, channelopathies, myotonic disorders, myotonic dystrophy (Steinert's disease), myotonia congenita (Thomsen's disease).

Particular examples of muscle disorders that could be treated with the subject cells include disorders of the heart muscle. Such disorders include, without limitation, myocardial infarction (interruption of blood supply to a part of the heart, causing heart cells to die); cardiac arrest (failure of the heart to contract effectively); heart failure (a progressive inability of the heart to supply sufficient blood flow to meet the body's needs, often but not always due to myocardial infarction or cardiac arrest); cardiac ischemia reperfusion injury (injury to a tissue due to reperfusion of the tissue with blood following an ischemic condition); cardiomyopathy (muscle weakness due to e.g. ischemia, drug or alcohol toxicity, certain infections (including Hepatitis C), and various genetic and idiopathic (i.e., unknown) causes); injury due to surgery, and degenerative heart diseases such as conduction disease and congenital defects.

In certain cases, the lineage restricted progenitor cells may be used to supplement the number of differentiated cell in a subject in whom there has been a decline in the number of differentiated cell due to aging, such as, a decrease in muscle mass, neurons, and the like.

Diseases other than those of the musculature may similarly be treated by regenerative tissue therapy that employs lineage-restricted cells produced by the subject methods. For example, diseases of the central nervous system (CNS) or the peripheral nervous system (PNS) may be treated by such therapy. For example, for the treatment of Parkinson's disease, dopaminergic neurons may be transiently induced to divide, giving rise to neural progenitors (i.e. mitotic cells of the neural lineage) or neural precursors (post-mitotic cells of the neural lineage, i.e. following exit from mitosis) that may be transferred into the substantia nigra of a subject suffering from Parkinson's disease. Alternatively, the neural progenitors or neural precursors may be induced to differentiate into dopaminergic neurons ex vivo, and then transferred into the substantia nigra or striatum of a subject suffering from Parkinson's disease. Alternatively, dopaminergic neurons of the substantia nigra of a subject suffering from Parkinson's disease may be induced to transiently divide in situ. Descriptions of post-mitotic differentiated neurons, neuronal progenitor and precursor cells, and methods for culturing these cells are have been described in the art. Other diseases and disorders of the nervous system that may benefit from the subject methods include Alzheimer's Disease, ALS, disorders of olfactory neurons, a disorder of spinal cord neurons, a disorder of peripheral neurons, and other disorders due to injury or disease.

For the treatment of multiple sclerosis, spinal cord injury, or other disorder of the central nervous system in which enhancing myelination is desirable to treat the disorder, oligodendrocytes may be induced to divide, giving rise to oligodendrocyte progenitors or oligodendrocyte precursors, which are then transferred to a subject suffering from a demyelinating condition of the CNS, e.g. multiple sclerosis or another condition where it is desirable to enhance myelination, e.g., spinal cord injury, etc. The lineage restricted progenitor cells may be transplanted at the site where enhanced myelination is desired. Alternatively, the oligodendrocyte progenitors or oligodendrocyte precursors may be induced to differentiate into oligodendrocytes ex vivo, and then transferred into the subject suffering from the MS, spinal cord injury, etc., at the site where enhanced myelination is desired. Alternatively, oligodendrocytes of a subject suffering from the MS, spinal cord injury, etc. may be induced to transiently divide in situ at the site where enhanced myelination is desired. Descriptions of post-mitotic differentiated oligodendrocytes, oligodendrocyte progenitors, and oligodendrocyte precursors, and how to culture these cells are described in Dugas, J. et al. (2006) J. Neurosci. 26:10967-10983 and US Application No. 20090258423.

In other examples, pancreatic islet cell progenitor or precursor cells generated from post-mitotic differentiated pancreatic islet cells may be transplanted into a subject suffering from diabetes (e.g., diabetes mellitus, type 1), see e.g., Burns et al., (2006) Curr. Stem Cell Res. Ther., 2:255-266. Descriptions of post-mitotic differentiated cells of the pancreas, i.e., islet cells, the progenitor and precursor cells of that lineage, and methods for culturing these cells are described in U.S. Pat. No. 6,326,201, the disclosure of which is incorporated herein by reference.

Hepatic progenitor cells or post-mitotic differentiated hepatic cells derived from post-mitotic differentiated hepatic cells are transplanted into a subject suffering from a liver disease, e.g., hepatitis, cirrhosis, or liver failure.

In some instances, it will be desirable to regenerate tissue with lineage-restricted cells that were produced from post-mitotic differentiated cells of allogeneic tissue, that is, tissue from a different host, for example, where the disease conditions result from genetic defects in tissue-specific cell function. Where the dysfunction arises from conditions such as trauma, the subject cells may be isolated from autologous tissue, and used to regenerate function. Autologous cells may also be genetically modified, in order to correct disease conditions resulting from genetic defects. Alternatively, where the dysfunction arises from conditions such as trauma, post-mitotic differentiated cells may be transiently induced to divide in situ, giving rise to lineage-restricted cells that will differentiate and incorporate into the injured tissue.

As alluded to above, genes may be introduced into the subject lineage-restricted cells that have been produced ex vivo for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the lineage-restricted cells, e.g. electroporation, calcium precipitated DNA, fusion, transfection, lipofection, infection and the like, as discussed above. The particular manner in which the DNA is introduced is not critical to the practice of the subject methods.

In Vitro Uses of Lineage-Restricted Progenitor Cells

Lineage-restricted progenitor cells may be used for generating cell lines that may be used for characterization of a disease. For example, differentiated cells may be obtained from a subject suffering from a disease that has not yet been well characterized. These cells may be used to generate lineage-restricted progenitor cells that also exhibit the disease phenotype. Thus, the propagated lineage-restricted progenitor cells may serve the characterization of the regulatory mechanisms that have been perturbed in the disease. In addition, these cells will serve as material on which to screen therapeutic agents for their ability to ameliorate the disease phenotype.

In screening assays for biologically active agents, lineage-restricted progenitor cells are produced from differentiated cells from an individual, e.g., an individual with a disease condition, e.g., a live individual or a cadaver, by the subject methods described above, and allowed to differentiate. The differentiated cells are then contacted with a candidate agent of interest and the effect of the candidate agent is assessed by monitoring amelioration of one or more phenotype of the disease.

Screening Methods

Methods for screening for an agent that inhibits tyrosine phosphatases and an agent that inhibits apoptosis and mediates generation of lineage-restricted progenitor cells from a differentiated cell are also provided. The method may include contacting a differentiated cell with a candidate agent that inhibits tyrosine phosphatases and a candidate agent that inhibits apoptosis under conditions sufficient for generation of lineage-restricted progenitor cells from the differentiated cell, wherein the differentiated cell and the have the same lineage; and determining whether lineage-restricted progenitor cells are produced, wherein the presence of lineage-restricted progenitor cells indicates that the candidate agent that inhibits tyrosine phosphatases and the candidate agent that inhibits apoptosis mediate generation of lineage-restricted progenitor cells from a differentiated cell.

Candidate agents of interest for screening include biologically active agents of numerous chemical classes, primarily organic molecules, although including in some instances, inorganic molecules, organometallic molecules, immunoglobulins, genetic sequences, etc. Also of interest are small organic molecules, which comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Compounds may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A plurality of assays may be run in parallel with different concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e., at zero concentration or below the level of detection of the agent or at or below the concentration of agent that does not give a detectable change in dedifferentiation and production of lineage-restricted progenitor cells or decrease in activity of tyrosine phosphatases or inhibition of caspases.

In certain cases, the differentiated cell is as provided above. In certain cases, the differentiated cell may be a myocyte and the lineage-restricted progenitor cells may be myogenic progenitor cells.

Kits

A kit for use in generation of lineage-restricted progenitor cells from a differentiated cell is also provided. The kit may include an agent that inhibits tyrosine phosphatases and an agent that inhibits apoptosis. The agents might be premixed in a single container or provided in separate containers.

In certain embodiments, the kit may include an inhibitor of tyrosine phosphatase and an inhibitor of caspases as described herein. In certain cases, the kit may include a vanadium containing small molecule and an general caspase inhibitor, such as, those described herein.

EXAMPLE

Materials and Methods

Animal Strains:

B6;129-Gt(ROSA)26Sor$^{tm1(rtTA*M2)Jae}$ Col1a1$^{tm2(tetOPou5f1)Jae}$/J strain (Stock Number: 006911), B6.129X1-Gt(ROSA)26Sor$^{tm1(EYFP)Cos}$/J strain (Stock Number: 006148), NOD.CB17-Prkdcscid/J (Stock Number: 001303) and C57BL6/J (2-3 months old) mice were obtained from pathogen free breeding colonies at The Jackson Laboratories. Animals were housed at the Northwest Animal Facility, University of California, Berkeley and procedures were performed in accordance to administrative panel on the Office of Laboratory Animal Care, UC Berkeley.

Reagents, Antibodies, Western Blotting and Immunofluorescence:

BpV(phen) (Alexis Biochemicals), Doxycycline (Sigma) and apoptosis inhibitor (Q-VD-OPh, Non O methylated Cat No. 551476, Calbiochem), BrdU (Sigma), ECM (Sigma), Hoechst 33342 (Sigma), DNase1 (Sigma), propidium iodide (molecular probes), Rnase A (Fermentas) and mouse bFGF (R&D) were purchased. Antibodies to BrdU (ab6326), GFP (ab6556 and ab13970), Ki67 (abcam ab155800) and Oct4 (ab18976) were from Abcam. Antibodies against Actin (rabbit polyclonal) were from Sigma, Pax7 was from DSHB (Develpmental Studies Hybridoma Bank), eMyHC from DSHB and Upstate, mouse monoclonal antibodies against Myogenin, MyoD and p21 were from Santa Cruz Biotechnology. For western blotting, the cells were lysed in RIPA buffer (50 mM Tris-Cl pH7.6, 150 mM NaCl, 0.1% SDS, 1%

NP-40, 0.25% sodium deoxycholate, 1 mM sodium orthovanadate, 1 mM NaF, 1 mM PMSF, 1 mM EDTA, 1× Protease inhibitor, Sigma) and protein concentration determined by Bradford Assay. 30 µg protein was run on precast 4-20% Gels (BioRad), then transferred to nitrocellulose membrane for 2 hours and protein expression detected by BioRad Gel Doc/Chemi Doc imaging system and Quantity One Software. For immunofluorescence, cells were fixed with 4% PFA for 15 minutes at room temperature followed by permeabilization with 0.25% Triton-X 100 for 12 minutes and blocked for one hour in blocking buffer (1% BGS+0.1% Na-Azide in 1×PBS) followed by primary antibody incubation in blocking buffer for 2 hours or overnight and secondary antibody incubation for 1 hour in blocking buffer with Alexa fluorophore conjugated species specific secondary antibody (Invitrogen). For BrdU labeling, cells were pulsed with 10 µM BrdU for either 2 or 24 hours, fixed with 4% PFA for 15 minutes, permeabilized with 0.25% Triton-X 100 for 12 minutes followed by DNase1 treatment (0.2 units/µL) for 30 minutes at room temperature. For all immunofluorescence, cells were mounted with mounting media containing DAPI (Prolong Gold Antifade, Invitrogen) to visualize nuclei in all immunostaining experiments.

Primary Myoblast Isolation:

Primary myoblasts were obtained by isolation of satellite cells from these mice as described previously (Conboy and Conboy, Methods Mol Biol 621, 149-163, 2010). TA and Gastrocnemius muscle of the different transgenic mice were injected with total 5 µg cardiotoxin (Sigma) dissolved in 1×PBS and muscle was dissected out after 3 day injury as described (Conboy and Conboy, Methods Mol Biol 621, 149-163, 2010). In brief, muscle underwent enzymatic digestion at 37° C. in DMEM (Cellgro)+1% Penicillin/Streptomycin+ 250 units/ml Collagenase Type II (Sigma) solution for one and half hour on rocker with slight agitation. Bulk myofibers were purified by repeated rounds of trituration, sedimentation and washing to remove interstitial cells, tendons etc. Satellite cells were purified from these bulk myofibers by incubation in 0.5 units/ml dispase at 37° C. for half an hour followed by sedimentation, washing, and fine mesh straining. The satellite cells were then cultured on 1:500 ECM (Sigma) coated plates in myoblast growth medium containing Ham's F-10 nutrient mixture (Gibco)+20% Bovine Growth Serum (BGS; Hyclone)+9 ng/ml bFGF (R&D)+1% Penicillin/Streptomycin. Later, proliferating fusion competent myoblasts were pre-plated to remove fibroblasts from culture.

Adenovirus Infection and Primary Myotube Labeling: Wild type MB or Tet-Oct4 MB obtained were infected with Ad-CMV-Cre or Ad-RFP control virus (Vector Biolabs) for 4-6 hours, washed off and cultured in GM for 24 hours. Ad-Cre MB were then lifted off the plates, counted and co-cultured with Lox-YFP myoblasts in differentiation inducing medium DMEM (Cellgro)+2% horse serum (Sigma)+1% Penicillin/Streptomycin (BD Falcon) on 12 well ECM coated plates. The 96 hour old myotubes were visualized for YFP expression, treated with different experimental conditions and photographed everyday using Zeiss epifluorescence microscope Axio Observer A.1 fitted with Zeiss EYFP filter (BP 500/20 FT515 BP 535/30) at 10× and 20× objective.

De-Differentiation Assay: WT myoblasts or Tet-Oct4 ($3\times10^5$) myoblasts upon 4-6 hour infection with 300 MOI of Ad-Cre virus were washed with growth medium twice to get rid of any residual virus and incubated for another 24 hours in growth medium at 37° C. in 5% $CO_2$ incubator. These myoblasts were then lifted off from the plates by addition of 1×PBS, counted ($3\times10^4$ cells/well) and co-cultured with $7\times10^4$ Lox-YFP myoblasts (obtained from B6.129×1-Gt (ROSA)26Sor$^{tm1(EYFP)Cos}$/J mice strain) per well in differentiation inducing medium DMEM (Cellgro)+2% horse serum+1% Penicillin/Streptomycin on 12 well (BD Falcon) on ECM (1:500) coated 12 well plates. Later, 96 hour old YFP$^+$ myotube cultures were treated with BpV (phen) (10 µM) along with apoptosis/caspase inhibitor (Q-VD-OPh) (10 µM) daily for 2 days with and without doxycycline (2 µg/ml) in differentiation medium. The inhibitors were then withdrawn and cells were switched to growth medium containing bFGF (9 ng/ml). The treated cells were fed fresh growth medium and bFGF everyday over a period of time and the morphology of YFP expressing myotubes was routinely visualized by epifluorescence microscope using YFP filter and photographed using 10× and 20× objectives. For live Hoechst staining, 4 µM of Hoechst was added everyday to YFP labeled myotube cultures, incubated for 10 minutes at 37° C. in 5% $CO_2$ incubator, washed off to remove unlabeled Hoechst and photographed.

Calculation of Myotube Reprogramming Efficiency: The labeled YFP$^+$ myotubes per well in 4 day old Cre-Lox myotube cultures were determined to be 2600. After inhibitor treatment, ~350 YFP$^+$ mononucleated cells were found in culture. Hence reprogramming efficiency was calculated as the percent of YFP$^+$ mononucleated cells out of the total number of labeled YFP$^+$ myotubes which was determined ~13.46%. Another method was based on the determination of Lox YFP myonuclei in labeled myotubes. As an average number of myonuclei present in each YFP$^+$ myotube is ~4 and for myotube labeling, Cre and Lox YFP myoblasts were cultured in ratio of 1:2 hence Lox YFP myonuclei were estimated to be ~6940 [(2600×4)×2/3]. Therefore, reprogramming efficiency calculated was the percent of YFP$^+$ mononucleated cells out of an estimated total number of Lox YFP myonuclei in YFP$^+$ myotubes and was determined ~5.04% [(350/6940)× 100] (see FIG. 11D).

Cell Transplantation: $1\times10^6$ reprogrammed YFP$^+$ mononucleated cells expanded in GM in culture were re-suspended in medium containing Ham's F-10 with 2% BGS and injected in 24 hours cardiotoxin pre injured Tibialis Anterior (TA) muscles of NOD-SCID mice (4 weeks old) obtained from Jackson lab. Control injections were performed with medium alone or Lox YFP myoblasts re-suspended in medium. After 2-3 weeks of cell injections, TA muscles were dissected out and fixed in 4% paraformaldehyde (PFA) for minimum of 2 hours and subsequently washed three times with 1×PBS for total of 45 minutes. The muscles were then sequentially transferred to 2%, 5% and 10% sucrose in PBS with slight agitation at room temperature for 30 minutes-1 hour. Finally muscles were left overnight in 20% sucrose at 4° C. and frozen in liquid nitrogen cooled iso-pentane in OCT embedding medium. 10 um muscle sections were cut and mounted on superfrost slides. 300 um serially spaced muscle sections from whole block were post-fixed with 4% PFA for 10 minutes and permeabilized for 10 minutes with 0.25% Triton X-100 and blocked in goat serum. Primary antibodies against YFP (chicken polyclonal GFP, Abcam) and laminin (rat laminin from Sigma) were added overnight followed by 1 hour incubation in the respective fluorochrome conjugated secondary antibodies (Goat anti Chicken 488 and Goat anti rat 546) from Molecular probes.

RNA Isolation and qRT-PCR: RNA isolation was performed by RNAeasy Kit (Qiagen) according to manufacture recommendations. For real time-qPCR, transcribed cDNA was diluted 1:5 for every sample and 1 µl of this diluted cDNA was used for 25 µl PCR reaction containing 80 nM forward and reverse primers, 12.5 µl of 2×1Q Syber Green mix (Bio-Rad), ran on iQ5 cycler (Bio-Rad) and data analyzed by iQ5 optical system software. The values normalized against internal control GAPDH and plotted using ΔΔCt method. The primers against specific genes for qRT-PCR are: GAPDH-F 5'-GGGAAGCCCATCACCATCT-3' (SEQ ID NO: 1) and GAPDH-R 5'-GCCTCACCCCATTTGATGTT-3' (SEQ ID NO: 2); Myogenin-F 5'-GACCCTACAGACGCCCACAA (SEQ ID NO: 3) and Myogenin-R-5'-CCGTGATGCTGTC-CACGAT-3' (SEQ ID NO: 4); MyoD-F 5'-CGGCTCTCTCT-GCTCCTTTG-3' (SEQ ID NO: 5) and MyoD-R-5'-GAGTC-GAAACACGGGTCATCA-3' (SEQ ID NO: 6); Pax7-F-5'-CCCTCAGTGAGTTCGATTAGC-3' (SEQ ID NO: 7) and Pax7-R-5'-CCTTCCTCGTCGTCCTCTTTC-3' (SEQ ID NO: 8); p21-F-5'GAACATCTCAGGGCCGAAAA-3' (SEQ ID NO: 9) and p21-R-5'-TGCGCTTGGAGTGATA-GAAATC-3' (SEQ ID NO: 10); eMyHC—F-5'-AGAG-GACGTGTATGCCATGA-3' (SEQ ID NO: 11) and eMyHC—R-5'-TGGCCATGTCCTCAATCTTGT-3' (SEQ ID NO: 12); Cre-recombinase-F-5'-GCCGGGTCA-GAAAAAATGG (SEQ ID NO: 13) and Cre recombinase-R-5'-AGGGCGCGAGTTGATAGCT-3' (SEQ ID NO: 14); eYFP F-5'-GCACGACTTCTTCAAGTCCGCCATGCC-3' (SEQ ID NO: 15) and eYFP R 5'-GCG GATCTTGAAGT-TCACCTTGATGCC-3' (SEQ ID NO: 16). Primers for p15 and p16 have been described elsewhere (Li et al., Nature 460, 1136-1139, 2009). For SA biosciences/Qiagen PCR arrays, 0.5 µg RNA was reverse transcribed using SA biosciences RT kit and PCR arrays carried out according to manufacture instructions. Web based PCR array data analysis tool of SA biosciences was utilized for data analysis.

Flow Cytometry: De-differentiated YFP+ mononucleated cells were lifted off the plates by addition of PBS and re-suspended in PBS+5% BSA, filtered through 40 uM filter (BD Falcon) to remove any aggregates and placed on ice. Cell sorting was performed on Cytopeia Influx sorter with gating on YFP+ population set by a comparison with negative control sample of Lox-YFP myoblasts. The sorted cells were replated on ECM coated tissue culture dishes containing myoblast growth medium with 9 ng/ml bFGF and assessed for different markers. For cell cycle analysis, de-differentiated cells were expanded in culture, pelleted down and fixed in ice cold 70% ethanol overnight at −20° C. Next day, cells were pelleted down at 1400 rpm for 5 minutes at 4° C. and ethanol was removed. Cells were washed once with ice cold 1×DPBS and re-suspended in DNA staining solution (RNase 0.1 mg/ml, Propidium iodide 2 µg/ml, 0.05% Triton X 100 in 1×DPBS) for 30 minutes at room temperature. The cells were pelleted down, washed once with ice cold DPBS and resuspended in DPBS+3% BSA for FACS analysis.

Statistical Analysis: p values were determined using student's t-test (2 samples equal variance, 2 tailed).

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Abbreviations

YFP, Yellow fluorescent protein; RFP, Red fluorescent protein, dox, doxycycline; DM, differentiation medium; GM, growth medium; BpV, bis-peroxovanadium; bFGF, basic fibroblast growth factor; eMyHC, embryonic myosin heavy chain; GAPDH, glyceraldehyde phosphate dehydrogenase; MB, myoblasts; MT, myotubes.

Overview

Muscle regeneration declines with aging and myopathies, and reprogramming of differentiated muscle cells to their progenitors can serve as a robust source of therapeutic cells. Here, the Cre-Lox method was used to specifically label post-mitotic primary multinucleated myotubes and then small molecule inhibitors of tyrosine phosphatases and apoptosis were utilized to de-differentiate these myotubes into proliferating myogenic cells, without gene over expression. The reprogrammed, fusion competent, muscle precursor cells contributed to muscle regeneration in vitro and in vivo and were unequivocally distinguished from reactivated reserve cells due to the lineage marking method. The small molecule inhibitors down-regulated cell cycle inhibitors and chromatin remodeling factors known to promote and maintain the cell fate of myotubes, facilitating cell fate reversal. These findings enhance understanding of cell-fate determination and create novel therapeutic approaches for improved muscle repair.

Example 1

Fusion-Dependent Lineage Marking of Primary Myotubes

Figure 2:
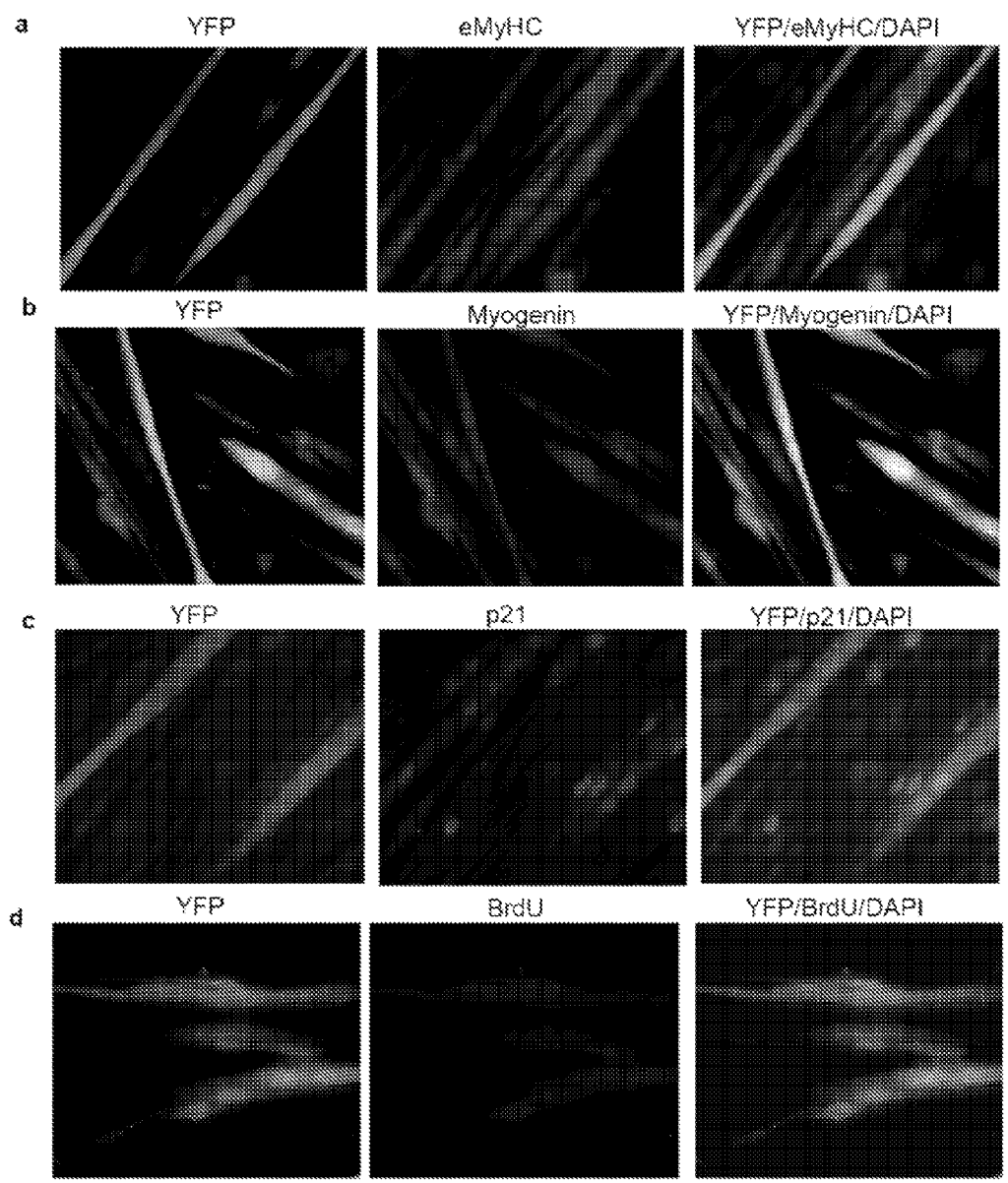
FIG. 2. Immunodetection of YFP and muscle specific markers.
Figure 10:
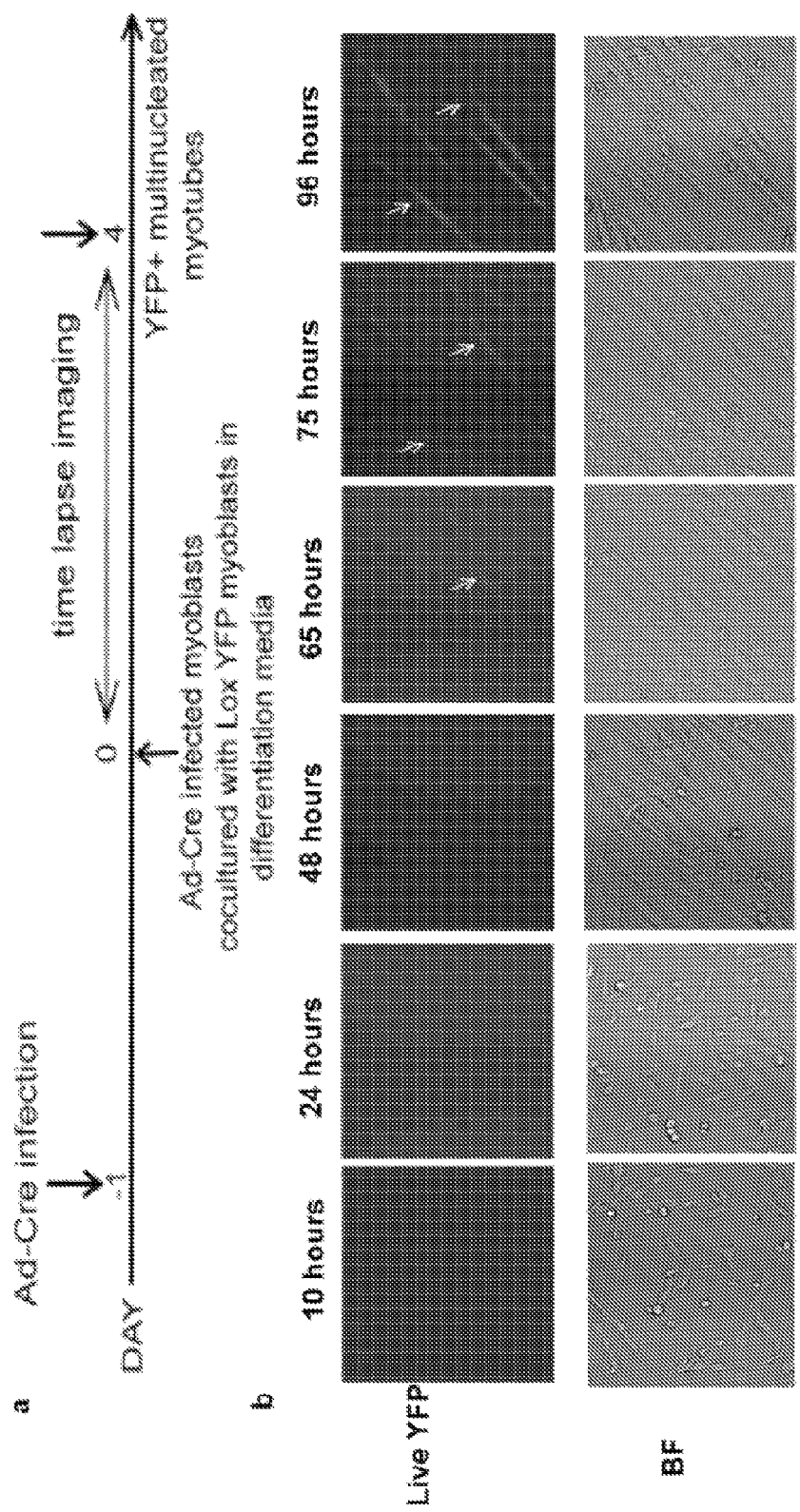
FIG. 10A-D. Representative images of time lapse microscopy are shown from labeling strategy captured by time lapse microscopy encompassing total number of 4 days from the co-culture of Cre and Lox YFP myoblasts to their fusion into multinucleated myotubes.
Figure 10:
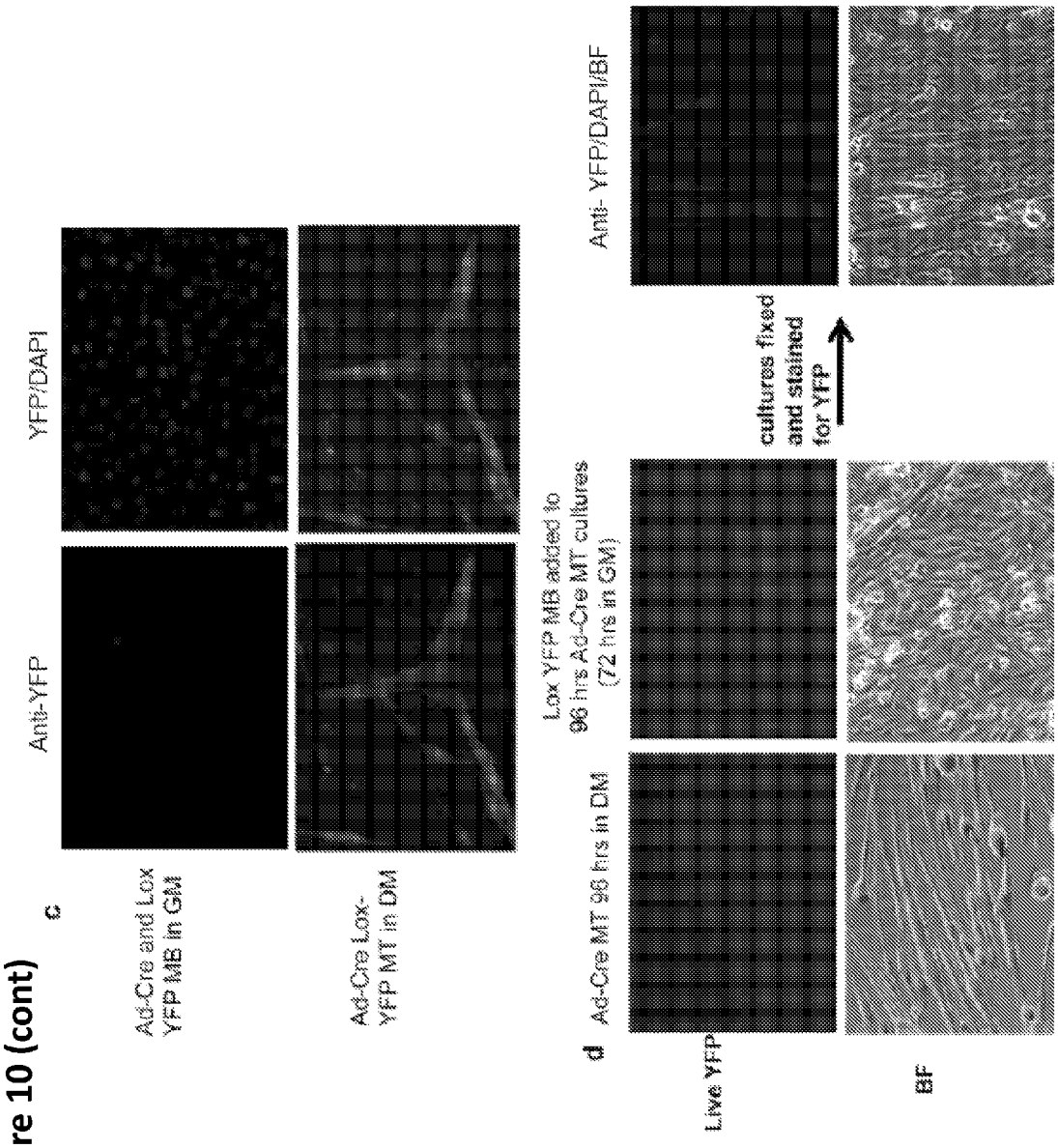

To overcome instances of mistaken cell identity during reprogramming studies, a method to genetically and irreversibly label terminally differentiated myotubes using the Cre-Lox technique was first established (FIG. 1A). The Cre-Lox system has been widely used for tissue specific disruption of genes, utilizing the P1 bacteriophage Cre recombinase which specifically recognizes Lox sites and excises any DNA sequence flanked by these sites (Nagy, 2000). The schematic of the system is represented in FIG. 1A. Cre recombinase was expressed exogenously by adenoviral mediated infection (Ad-Cre) in wild type primary myoblasts (MB). Ad-Cre infected myoblasts (Cre-MB) were co-cultured with Lox-YFP myoblasts (Lox-YFP MB) derived from Rosa26 YFP reporter mice (Srinivas et al., BMC Dev Biol 1, 4, 2001) in the ratio of 1:2 so that more number of Lox YFP myonuclei coexist with Ad-Cre myonuclei in single myotube and yield high expression of YFP. In standard low mitogen differentiation-promoting medium (DMEM, 2% horse serum), these co-cultured MB within 72-96 hours physiologically fused into YFP expressing myotubes (hence forth, YFP+ myotubes) where both Cre and Lox-YFP myonuclei co-existed (FIG. 1B). No mononucleated cells expressing YFP were observed, thus confirming the validity of this lineage marking strategy. Adenoviral infection control was also performed by co-culturing Ad-RFP infected MB with Lox-YFP MB in differentiation medium (DM) and this did not yield YFP+ myotubes (FIG. 1B). The YFP+ myotubes accounted for around 70% of total myotubes formed within 96 hours. Of these, around 60% of YFP+ myotubes, had 2-4 myonuclei, while 30% had 5-7 myonuclei with an average number of 4.5 myonuclei per YFP+ myotube. Non-YFP myotubes that arose from syngeneic fusion events of Cre-MB or Lox-YFP MB were also detected. This labeling strategy was captured by time lapse microscopy encompassing total number of 4 days from the co-culture of Cre and Lox YFP myoblasts to their fusion into multinucleated myotubes Representative images of time lapse microscopy are shown in FIG. 10. To further rule out any possibility of YFP expression without physiological myoblast fusion specific control experiments were conducted. The Cre-MB were co-cultured with Lox-YFP MB in mitogenic growth medium (GM; Ham's F10, 20% BGS, 9 ng/ml bFGF-2) where cells remained mononucleated and did not fuse into myotubes (FIG. 1B). After 96 hours of co-culture in GM, cells were processed for western blotting (FIG. 1C), qRT-PCR analysis (FIG. 1D) and immunostaining (FIG. 10) for YFP expression. No YFP expression was observed by any of these techniques. A more stringent control experiment was performed to check the possibility of horizontal transfer of Cre recombinase, without complete fusion process. For this, Cre myoblasts were cultured in differentiation medium to form myotubes. Later, LoxYFP MB ($2\times10^5$ cells) were added to 96 hour old Cre expressing myotubes and cultures switched to mitogenic growth medium for 72-96 hours. As seen in FIG. 10E, both epifluorescent imaging and anti-YFP staining confirmed the absence of YFP expressing mononucleated cells without physiological fusion of Cre-MB and Lox-YFP MB into myotubes. These results clearly show that indeed $YFP^+$ myotubes arose only from the fusion of Cre and Lox-YFP MB in DM. The results obtained and quantified with YFP live-direct fluorescence were completely consistent with the data produced using anti-YFP immuno-fluorescence and both assays were routinely employed throughout these studies. The $YFP^+$ myotubes were positive for muscle differentiation markers myogenin and eMyHC, and for CDK inhibitor, p21 (which indicates the post-mitotic state) (FIG. 2A-C). Furthermore, these $YFP^+$ myotubes did not incorporate BrdU, confirming that all $YFP^+$ marked cells produced by fusion of Cre and Lox-YFP MB have exited cell cycle and are in post-mitotic arrest by 96 hours in DM (FIG. 2D). These findings establish an unambiguous lineage marking of terminally differentiated myotubes that is dependent on physiological myoblast fusion.

Example 2

Figure 3:
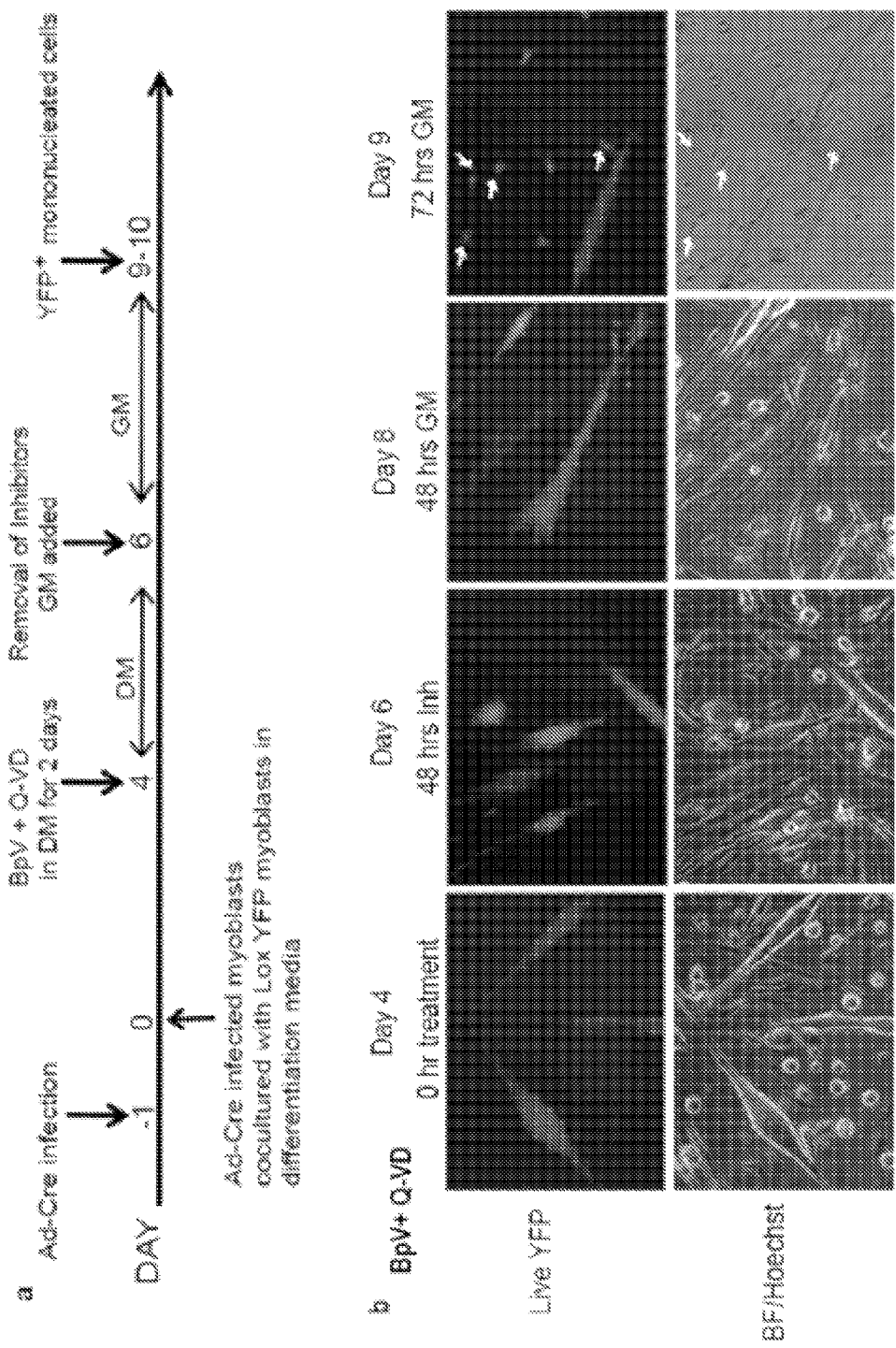
FIG. 3. BpV with Q-VD de-differentiates the irreversibly-labeled YFP$^+$ myotubes to YFP$^+$ proliferating mononucleated cells.
Figure 3:
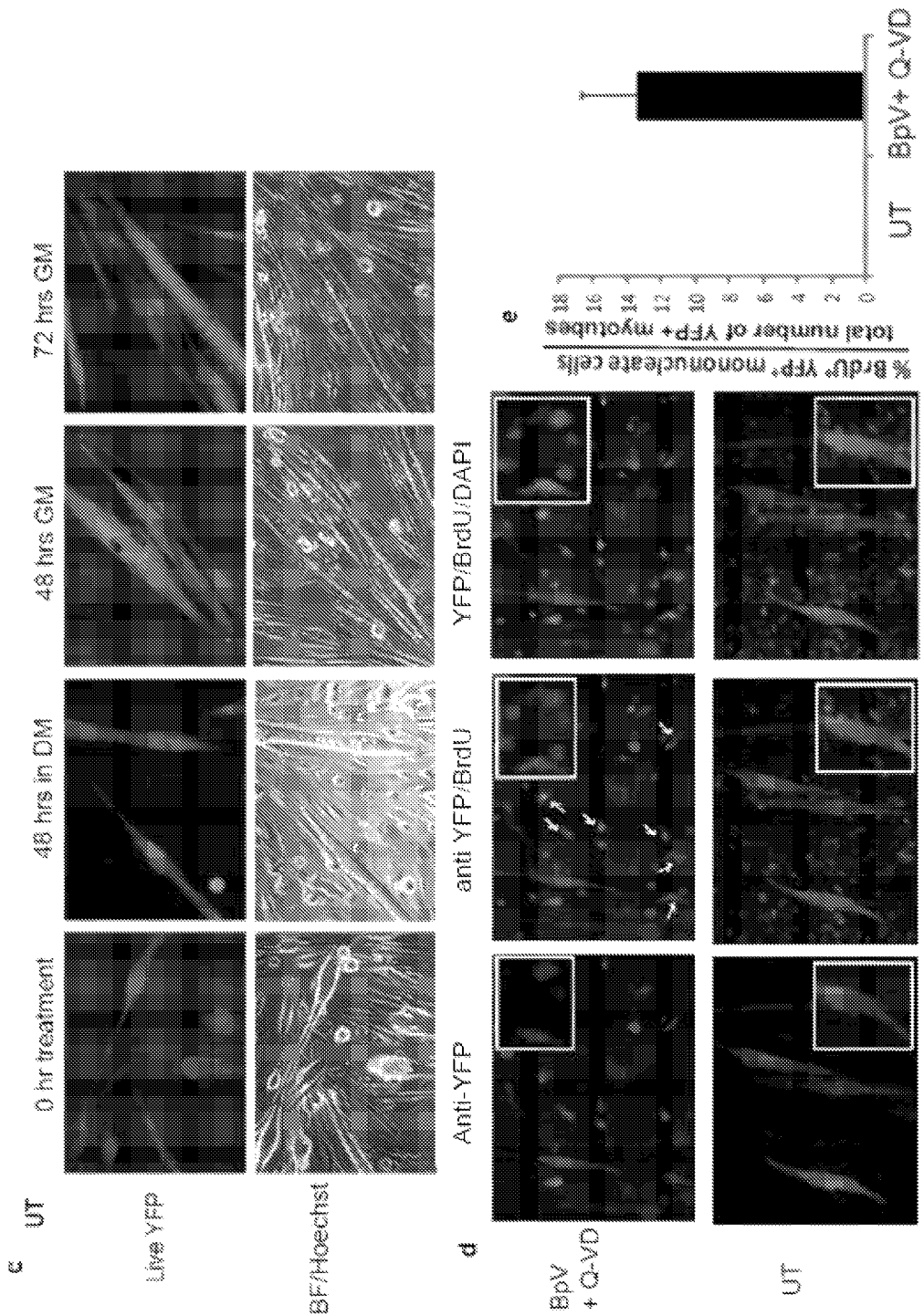
Figure 11:
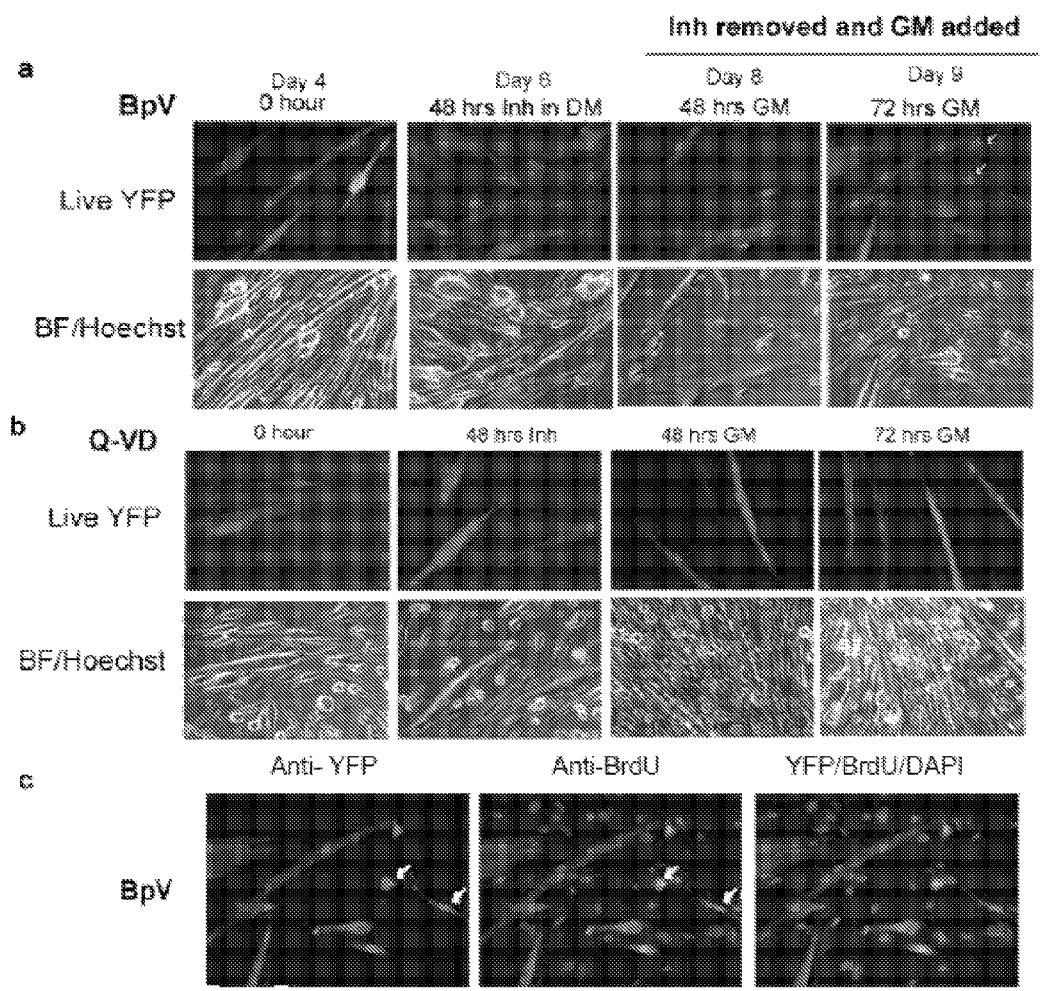
FIG. 11. Results demonstrate that the inhibition of apoptosis is a factor for the de-differentiation of multinucleated primary myotubes.
Figure 11:
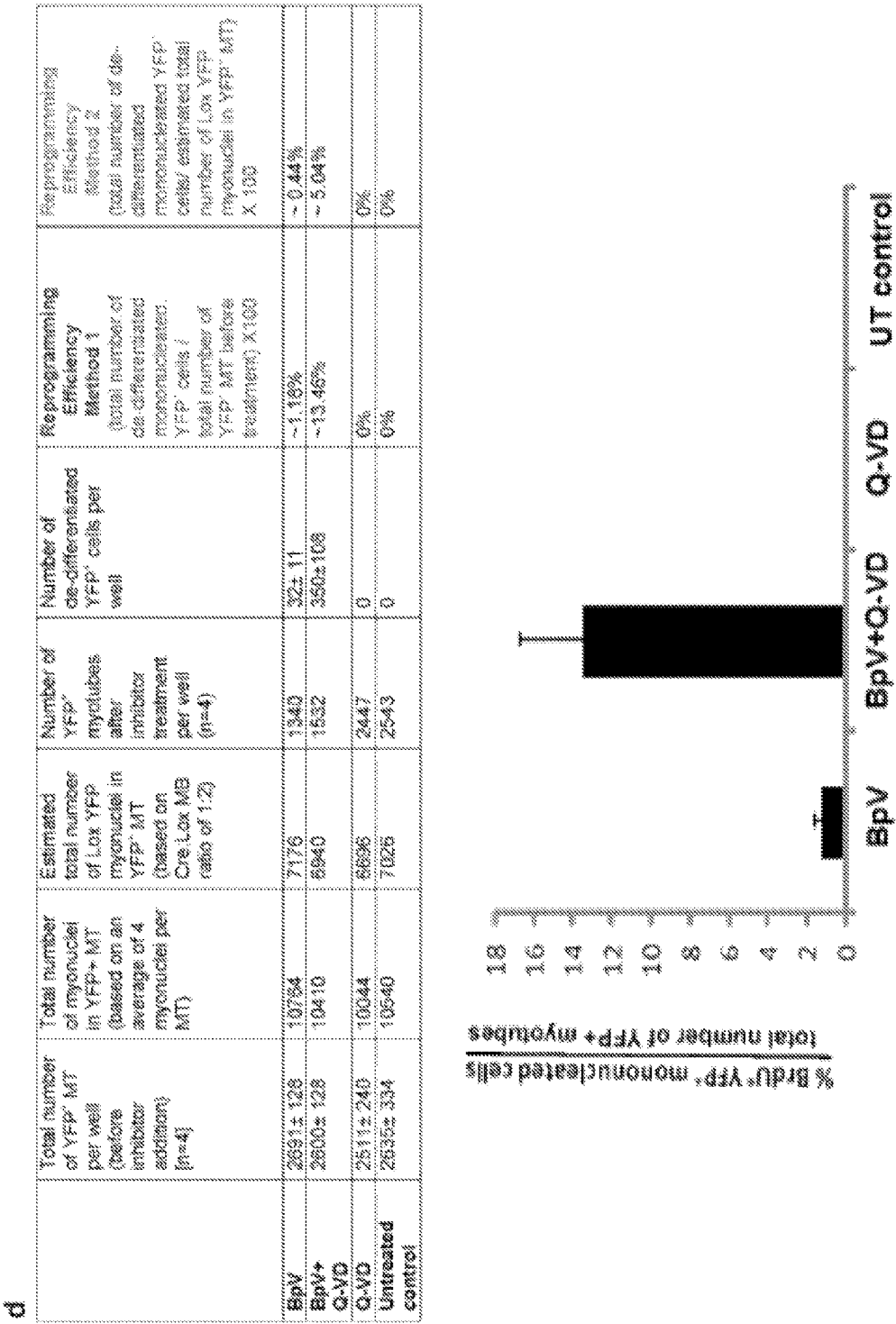
Figure 12:
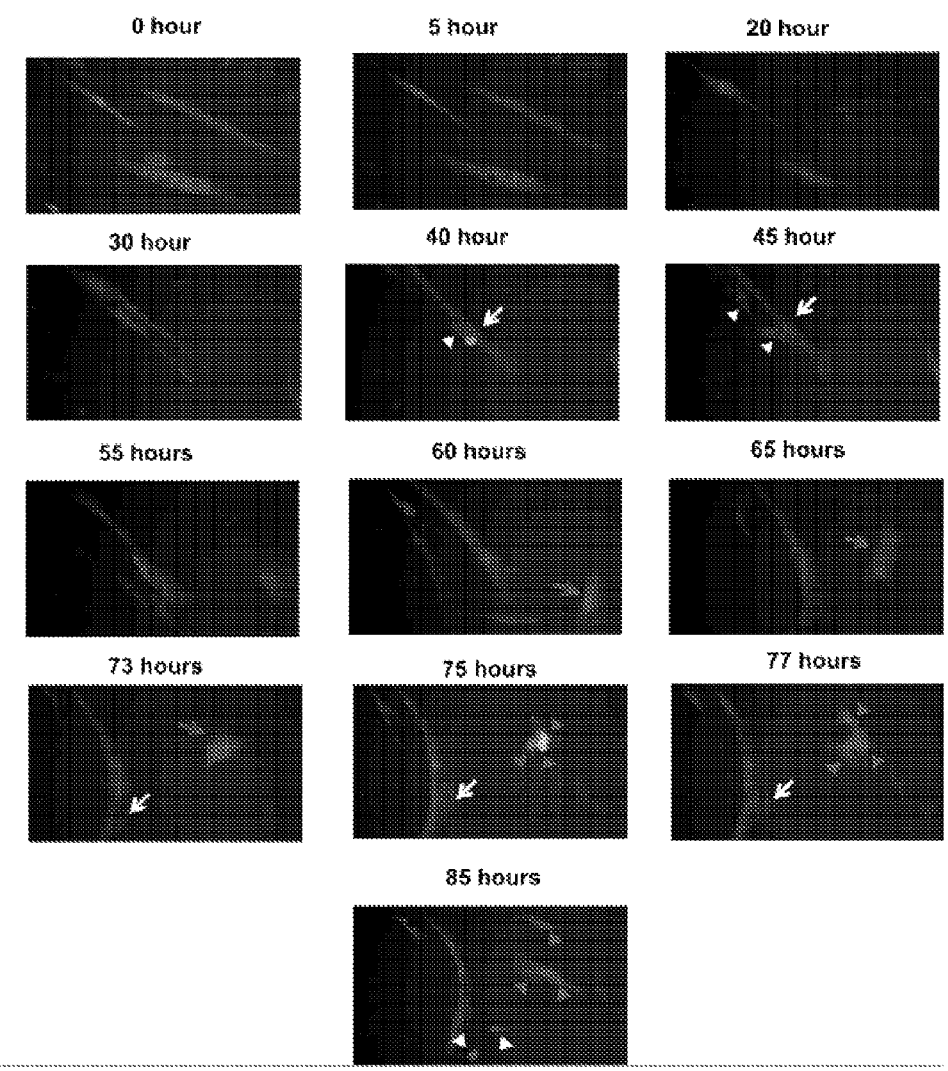
FIG. 12. Representative images of the time lapse imaging can be seen from live cell imaging performed for the total period of 4 days where inhibitor mix treated YFP$^+$ multinucleated myotubes gave rise to YFP$^+$ mononucleated cells.
Figure 13:
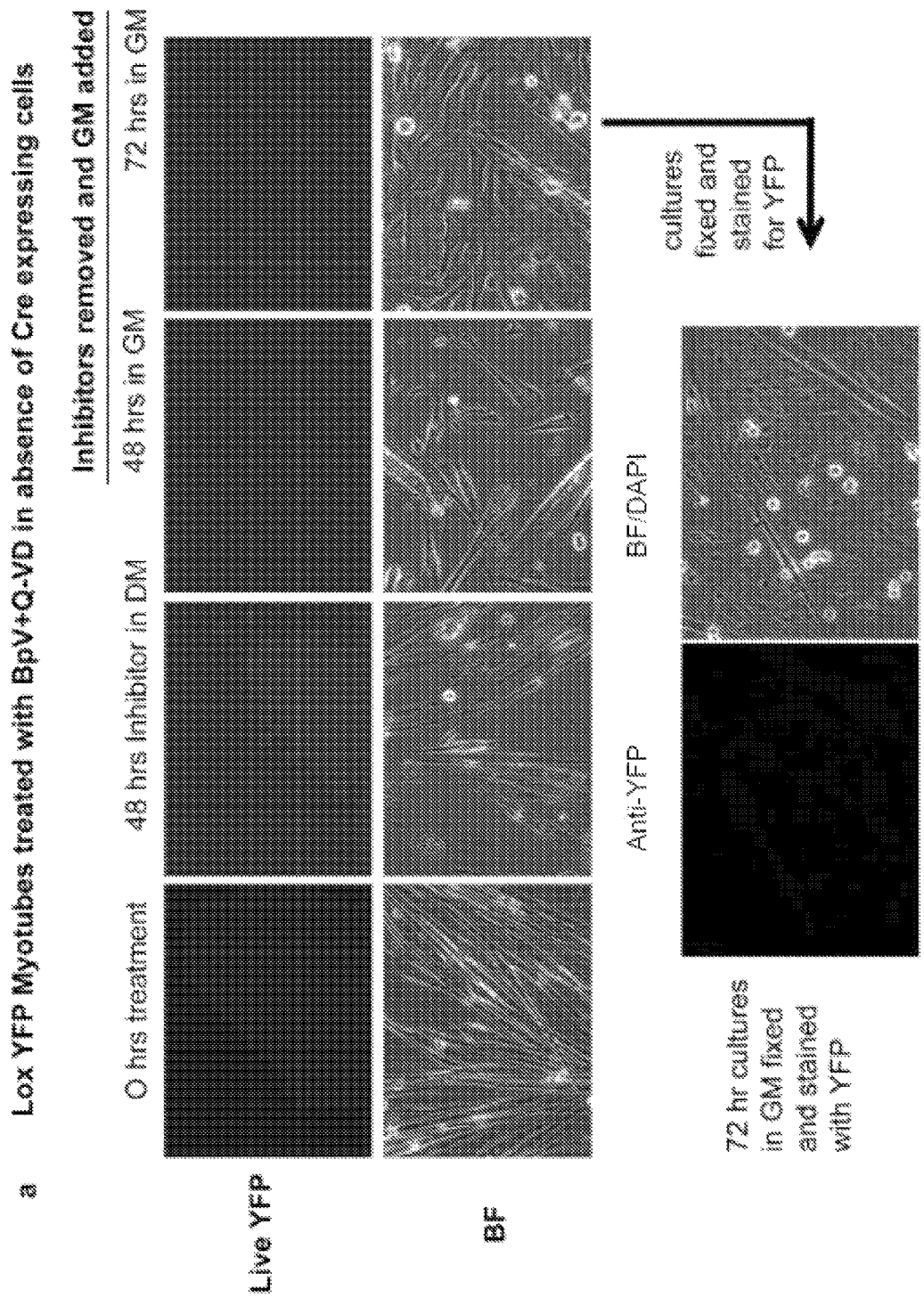
FIG. 13.
Figure 13:
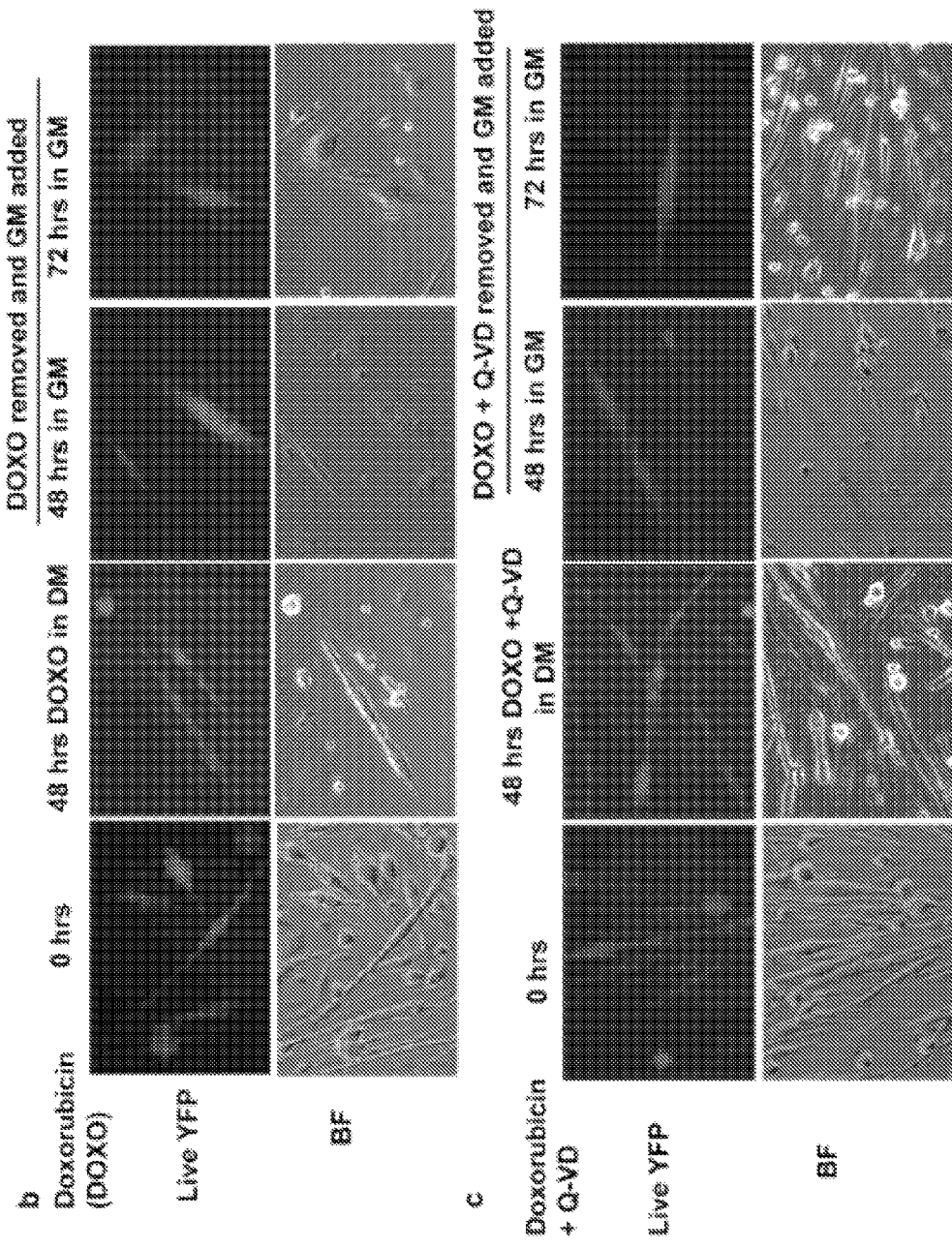

Inhibition of Tyrosine Phosphatase and Apoptosis Reprograms Myotubes into Proliferating Mononucleated Cells Myotube formation involves many events such as changes in cytoskeletal assembly, sequential expression of differentiation specific genes, modulation of signaling pathways and up-regulation of tyrosine phosphatases (Bennett and Tonks, Science 278, 1288-1291, 1997; Delgado et al., Genomics 82, 109-121, 2003; Lassar et al., Curr Opin Cell Biol 6, 788-794, 1994; Weintraub, Cell 75, 1241-1244, 1993). Hence we reasoned that global transient inactivation of tyrosine phosphatases would reset signaling in myotubes, making them receptive to mitogens present in growth medium conditions and propelling them into cell cycle as well as towards less differentiated state. Earlier BpV (a tyrosine phosphatase inhibitor) was reported to delay differentiation of dividing C2C12 into myotubes (Castaldi et al., FASEB J 21, 3573-3583, 2007) and other studies also indicated that a small percentage of myotubes that enter S-phase upon over-expression of genes fail to proliferate and succumb to apoptosis (Endo and Nadal-Ginard, J Cell Sci 111 (Pt 8), 1081-1093, 1998; Latella et al., Cell Death Differ 7, 145-154, 2000). Therefore, we reasoned that if BpV was able to trigger the process of myotube de-differentiation and that the addition of an apoptosis inhibitor (Q-VD) in our studies may help in survival of those myotubes that might undergo massive restructuring of cell cytoskeleton simultaneously with the breakage of post-mitotic arrest. Using our lineage marking technique for myotubes, we then explored whether BpV+Q-VD (henceforth inhibitor mix) was capable to reprogram already differentiated primary myotubes to their muscle progenitor fate. For de-differentiation assays, inhibitor mix (10 μM each) was added to $YFP^+$ myotube cultures daily for two days after which cultures were switched to GM (FIG. 3A). Remarkably, in the presence of inhibitor mix, considerable number of $YFP^+$ myotubes showed altered morphology and cleaved into small cells which were followed by the appearance of $YFP^+$ mononucleated progeny of the de-differentiated myotubes (FIG. 3B). When myotubes produced by the fusion of primary myoblasts were treated with BpV alone, cell death occurred as described in previous studies (Rumora et al., 2003). Interestingly, in the presence of BpV alone, myotubes did show apoptosis and few of them gave rise to YFP+ mononucleated cells albeit at very low frequency (~1.18%) in comparison to inhibitor mix treatment which augmented the de-differentiation frequency to around ~12%-13% (FIGS. 11A, 11C and 11D). These results demonstrate that the inhibition of apoptosis is a factor for the de-differentiation of multinucleated primary myotubes. In control experiments, no $YFP^+$ mononucleated cells were observed in untreated $YFP^+$ myotubes that were switched to GM for 72 hours (FIG. 3C), or in the presence of Q-VD alone (FIG. 11B). Furthermore, the $YFP^+$ cells derived from the post-mitotic multinucleated myotubes engaged in proliferation, where ~12%-13% of total lineage marked population was found to incorporate BrdU during a 24 hour BrdU labeling interval (FIGS. 3D and 3E). The former myotube identity of these $YFP^+$ cells clearly discriminated them from the reactivation of reserve $YFP^-$ myoblasts, which also proliferated and expanded when myotube cultures were switched to the highly mitogenic GM (FIG. 3D). To rule out any spurious YFP expression in the absence of Cre expressing cells and in the presence of inhibitor mix, 4 day old Lox YFP myotube cultures were treated with the inhibitor mix and then switched to growth medium. No YFP expression was ever observed in these cultures. This shows that Lox YFP cells do not spontaneously express YFP upon addition of inhibitor mix in the absence of Cre recombinase (FIG. 13A). To capture reprogramming of lineage marked myotubes, we also performed time lapse microscopy where Ad-Cre-Lox YFP myotubes were labeled for 96 hours followed by the addition of inhibitor mix for another 48 hours and the cultures were then switched to GM. Live cell imaging was performed for the total period of 4 days where inhibitor mix treated $YFP^+$ multinucleated myotubes gave rise to $YFP^+$ mononucleated cells. Representative images of the time lapse imaging can be seen in FIG. 12. A combination of a small molecule tyrosine phosphatase inhibitor, BpV and an apoptosis inhibitor, Q-VD was sufficient for such reprogramming of terminally differentiated muscle cells. Since, inhibitor of tyrosine phosphatases induces apoptosis, the possibility that some aspect of apoptosis may mediate the reprogramming of multinucleated myotubes to undergo de-differentiation was also examined. 0.2 uM doxorubicin, a classic inducer of apoptosis which has been studied in muscle (Latella et al., 2004) was added to Cre-Lox myotube cultures for 48 hours either alone or in combination with the apoptosis inhibitor. This was followed by removal of drugs and switching cultures to growth media conditions for 72-96 hours. We observed reduced apoptosis by doxorubicin in the presence of apoptosis inhibitor but no $YFP^+$ mononucleated cells were observed in these cultures in spite of altered morphology of myotubes (FIGS. 13B and 13C). These suggests that apoptosis does not mediate the de-differentiation of myotubes.

Figure 14:
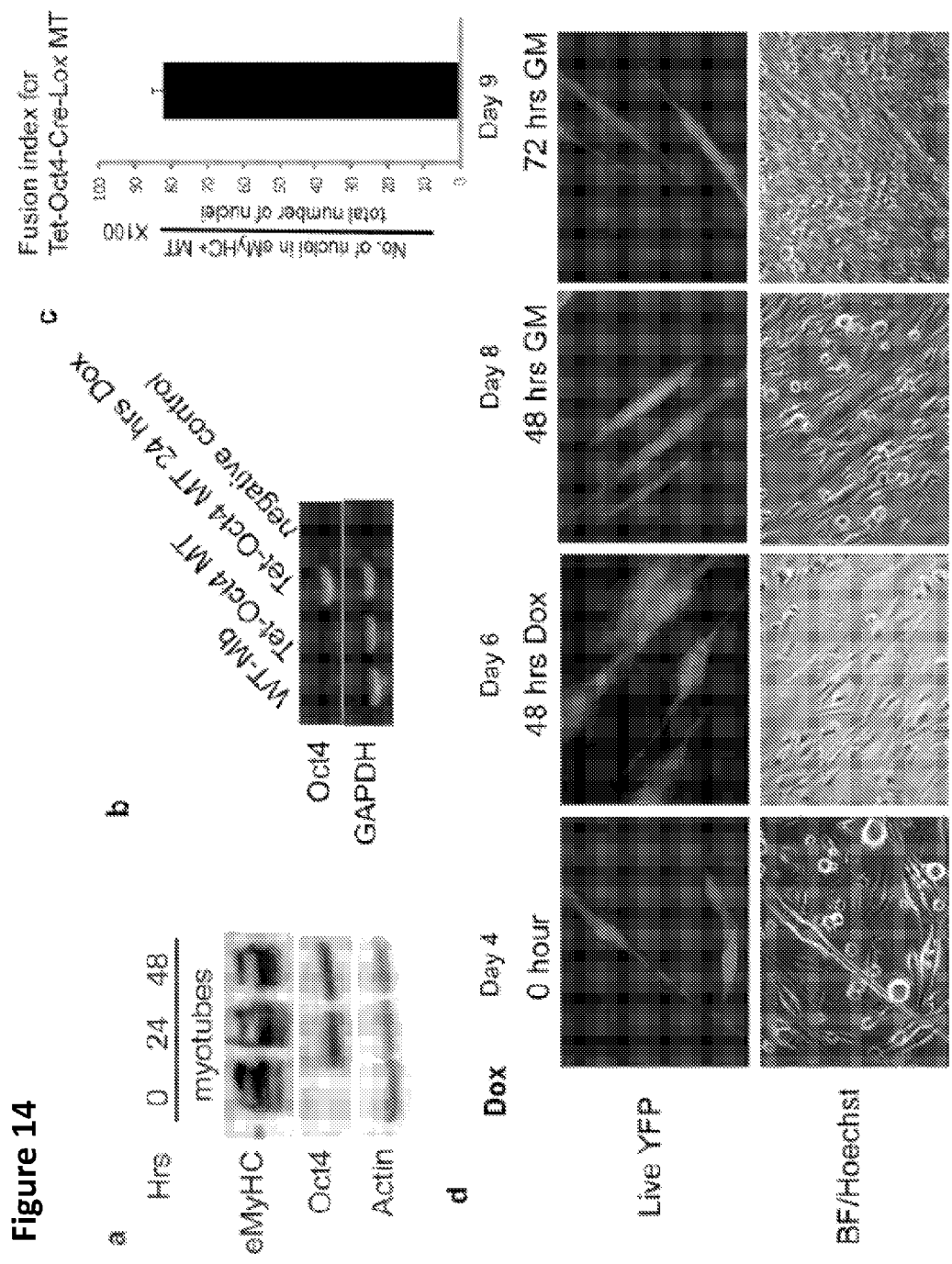
FIG. 14A-D. Tet-Oct4 myoblasts were infected with Ad-Cre and co-cultured with Lox-YFP MB in DM for 96 hours, where myotubes were readily formed.

In parallel to these experiments, we also addressed a possible role of Oct4 in myotube reprogramming considering the pivotal reprogramming activity of Oct4 and the ability of this transcriptional factor alone to reprogram neural stem cells (Kim et al., Nature, 2009). We used our published method (Conboy and Conboy, Methods Mol Biol 621, 149-163, 2010) to activate endogenous muscle stem (satellite) cells by injury into hind limb muscle of Tet-Oct4 mice (Hochedlinger et al., Cell 121, 465-477, 2005) and derived primary myoblasts which were kept in DM to form myotubes and then treated or untreated with doxycycline (dox) for 24 and 48 hours, to induce Oct4 protein and mRNA expression (FIG. 14). These Tet-Oct4 myoblasts were infected with Ad-Cre and co-cultured with Lox-YFP MB in DM for 96 hours, where myotubes were readily formed (FIG. 14). No significant changes in morphology of myotubes were observed up to 48 hours of Oct4 induction followed by growth media incubation for additional 4 days (FIG. 14D). In concert with earlier studies, where it has been reported that induction of Oct4 in the differentiated cells of the intestine and hair follicle has no effect on their cellular phenotype (Hochedlinger et al., supra, 2005), our results showed that Oct4 induction up to 2 days was not sufficient to induce any morphological changes in myotubes or to promote their de-differentiation in GM (FIG. 14D).

Example 3

Figure 4:
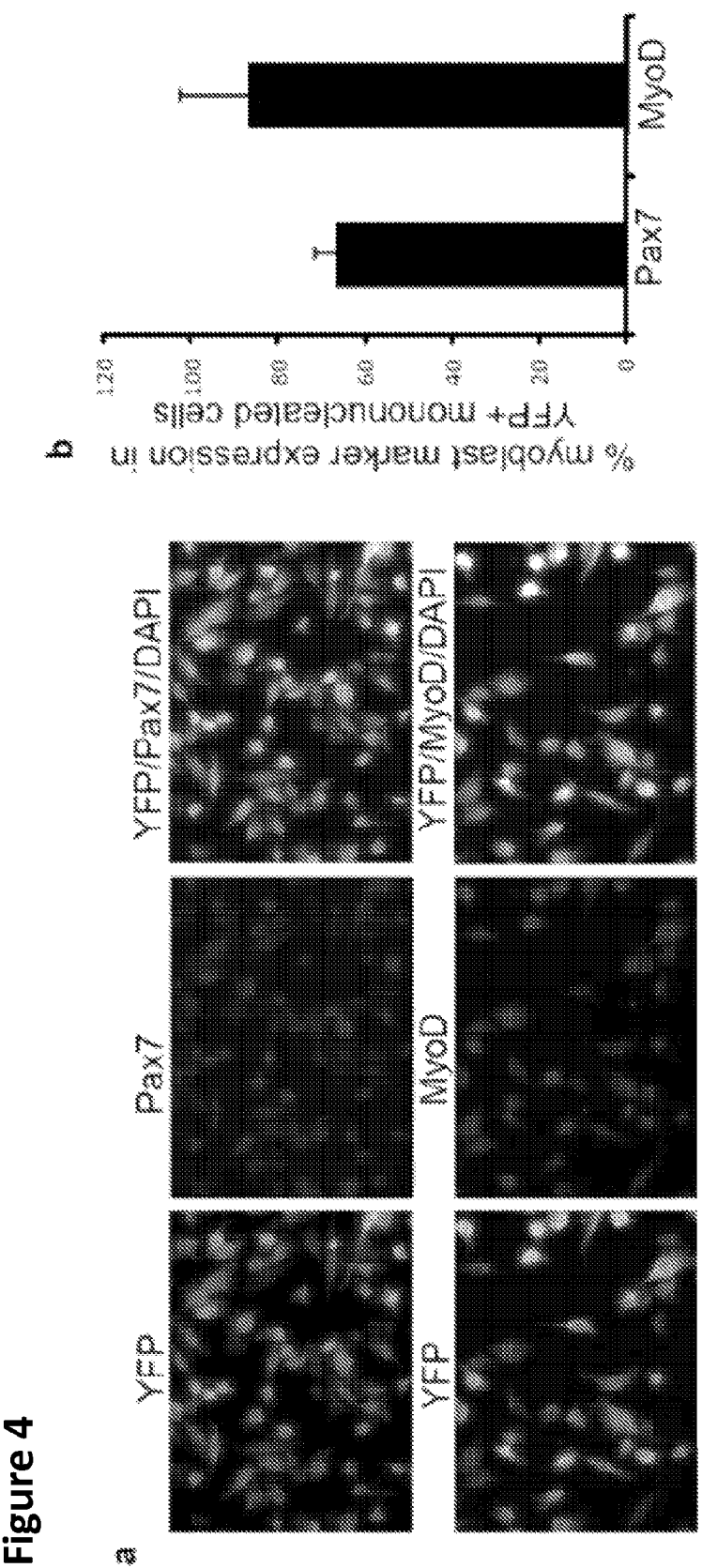
FIG. 4. Genetically-labeled progeny of de-differentiated myotubes have functional and genetic attributes of muscle progenitor cells.
Figure 4:
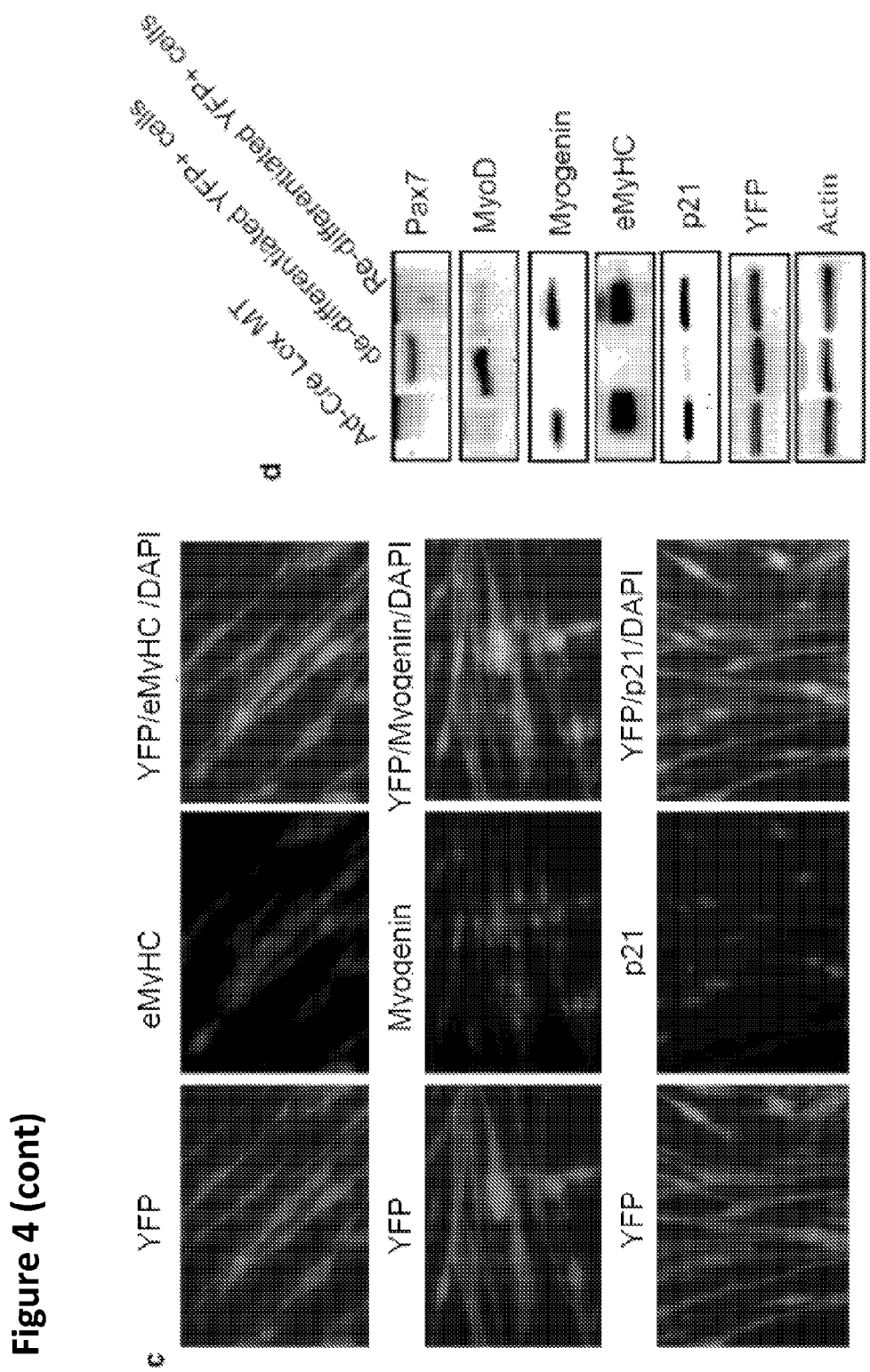
Figure 4:
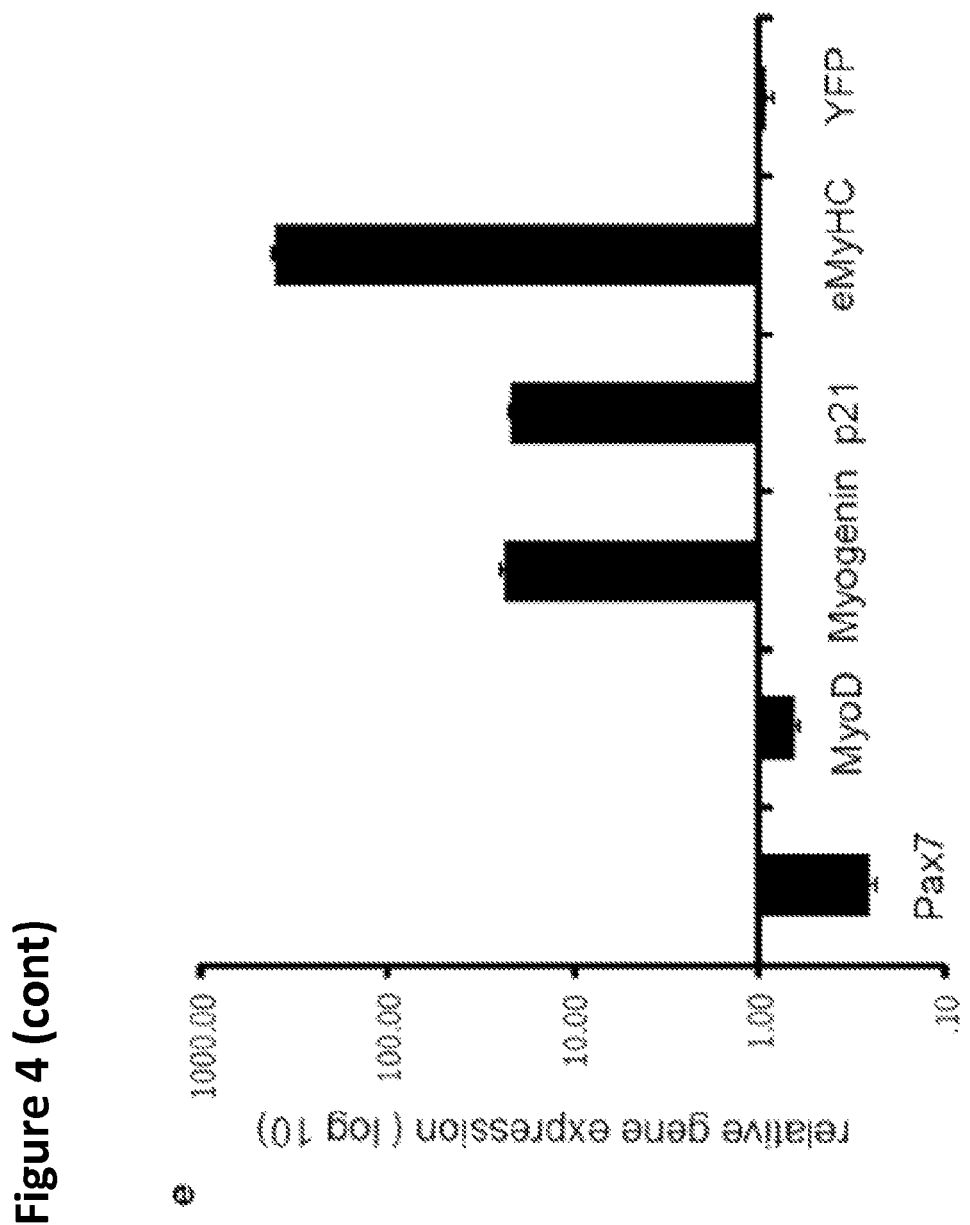
Figure 15:
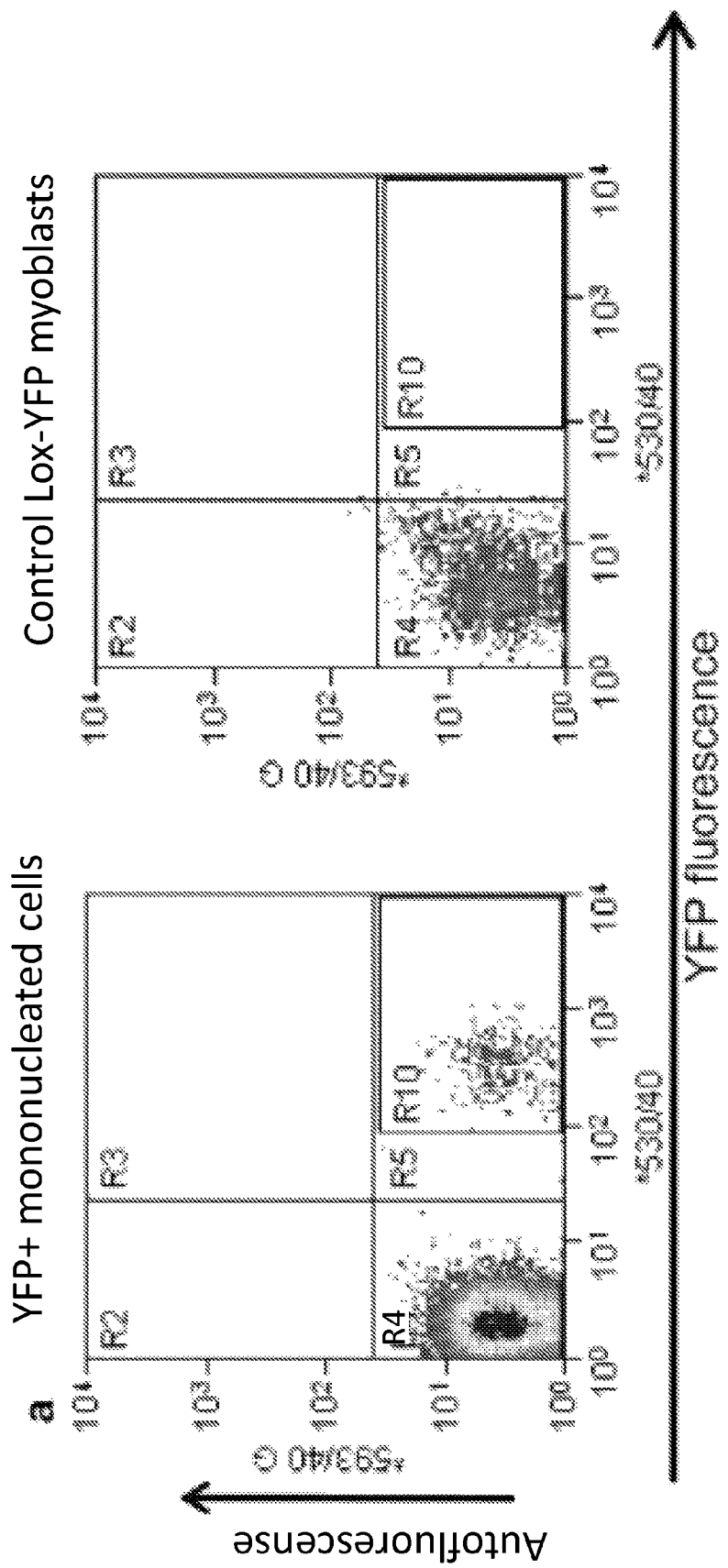
FIG. 15A-E. To further assess the properties of reprogrammed cells, mono-nucleated YFP$^+$ progeny of de-differentiated myotubes was FACS sorted and expanded in culture. These YFP$^+$ mononucleated cells were immunostained with antibody against Ki67 (proliferation marker) and BrdU (S phase marker) along with YFP.
Figure 15:
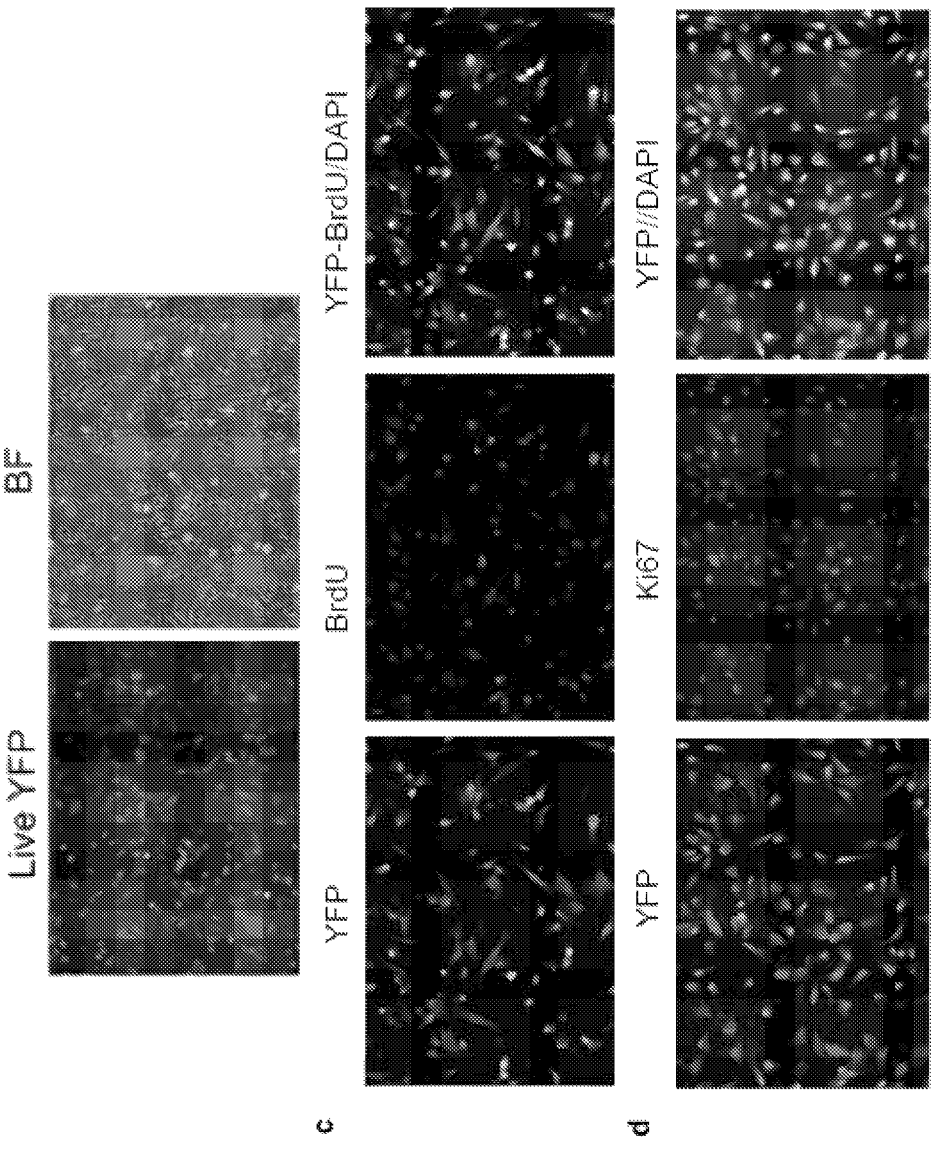
Figure 15:
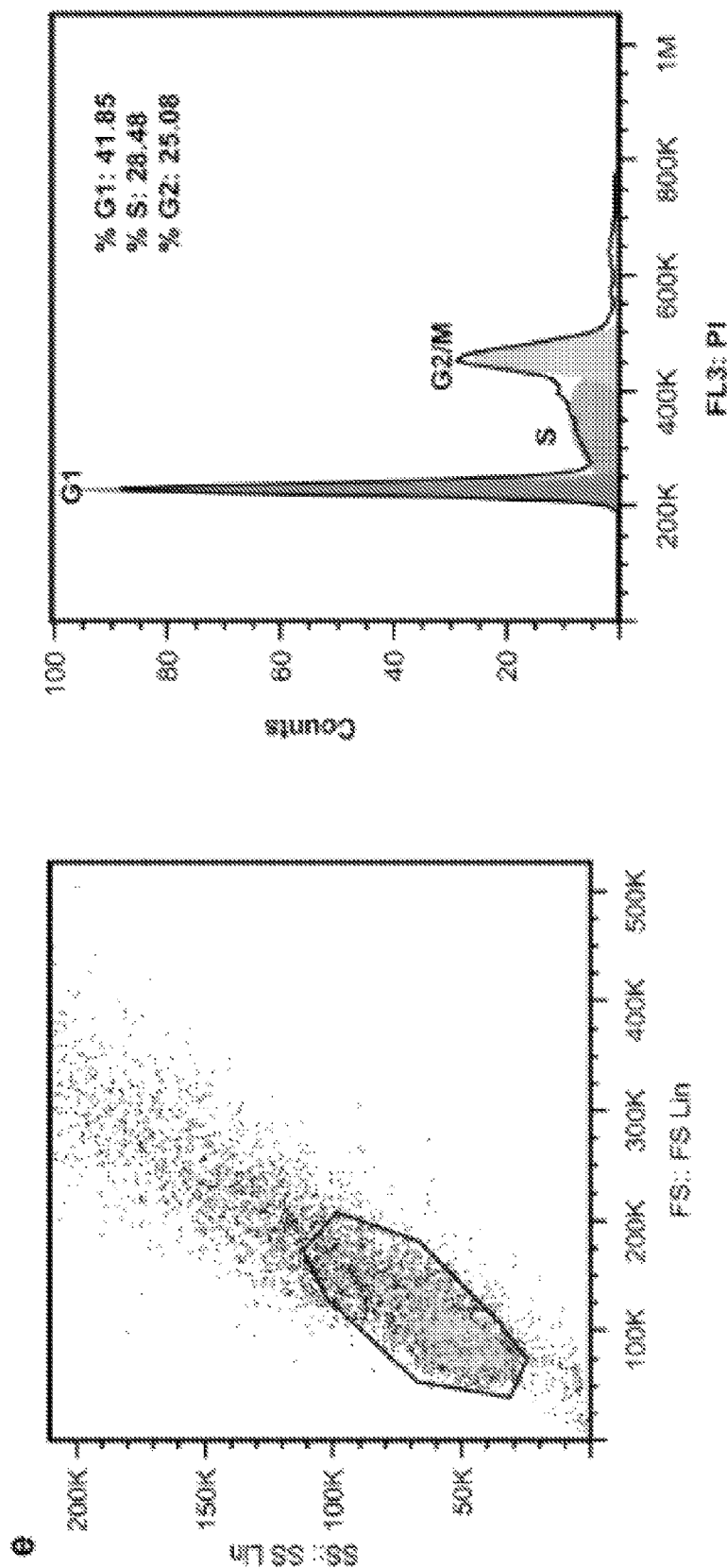

Mononucleated Cells Generated from De-Differentiated Myotubes Exhibit Hallmarks of Myogenic Progenitors To further assess the properties of reprogrammed cells, mono-nucleated YFP$^+$ progeny of de-differentiated myotubes was FACS sorted and expanded in culture (FIGS. 15A and 15B). These YFP$^+$ mononucleated cells were immunostained with antibody against Ki67 (proliferation marker) and BrdU (S phase marker) along with YFP. As shown in FIGS. 15C and 15D, these FACS sorted expanded YFP+ cells positively immunostained for Ki67 and incorporated BrdU. Further, cell cycle analysis by propidium iodide DNA staining confirmed that these cells can proliferate and exist in different phases of cell cycle (FIG. 15E). To confirm that the actively dividing reprogrammed YFP$^+$ cells are indeed myogenic, they were analyzed for the myogenic markers Pax7, MyoD1 and differentiation markers myogenin, eMyHC and Cdk inhibitor, p21 (FIG. 4A). Based on the quantification of the immunofluorescence, around 70% of YFP$^+$ mononucleated cells expressed high levels of Pax7 and ≥90% expressed MyoD1 (FIG. 4B). The differentiation capability of the YFP$^+$ mononucleated cells was tested by switching the cultures to DM where normal primary myoblasts exit cell cycle and fuse into multinucleated myotubes. The YFP$^+$ precursor cells were found to retain their myogenic potential as they underwent rapid physiological fusion de-novo into myotubes that expressed typical muscle differentiation markers, eMyHC and myogenin and p21 (FIG. 4C) Thus, the markers of terminal differentiation that were down-regulated upon myotube reprogramming with inhibitor mix treatment, were up-regulated again when YFP$^+$ myogenic progenitor cells differentiated into de-novo myotubes in the mitogen-low differentiation medium (FIG. 4D). The changes in marker gene expression was also validated at transcriptional level by qRT-PCR which clearly showed the up-regulation of eMyHC, p21 and myogenin and down regulation of Pax7 and MyoD mRNA levels upon differentiation of YFP$^+$ mono-nucleated cells (FIG. 4D). Thus, based on the profile of myogenic markers and the functional properties, de-differentiated genetically labeled progeny of primary myotubes acquired the fate of muscle precursor cells or myoblasts.

Example 4

Reprogrammed Progenitor Cells Contribute to In Vivo Muscle Regeneration

Figure 5:
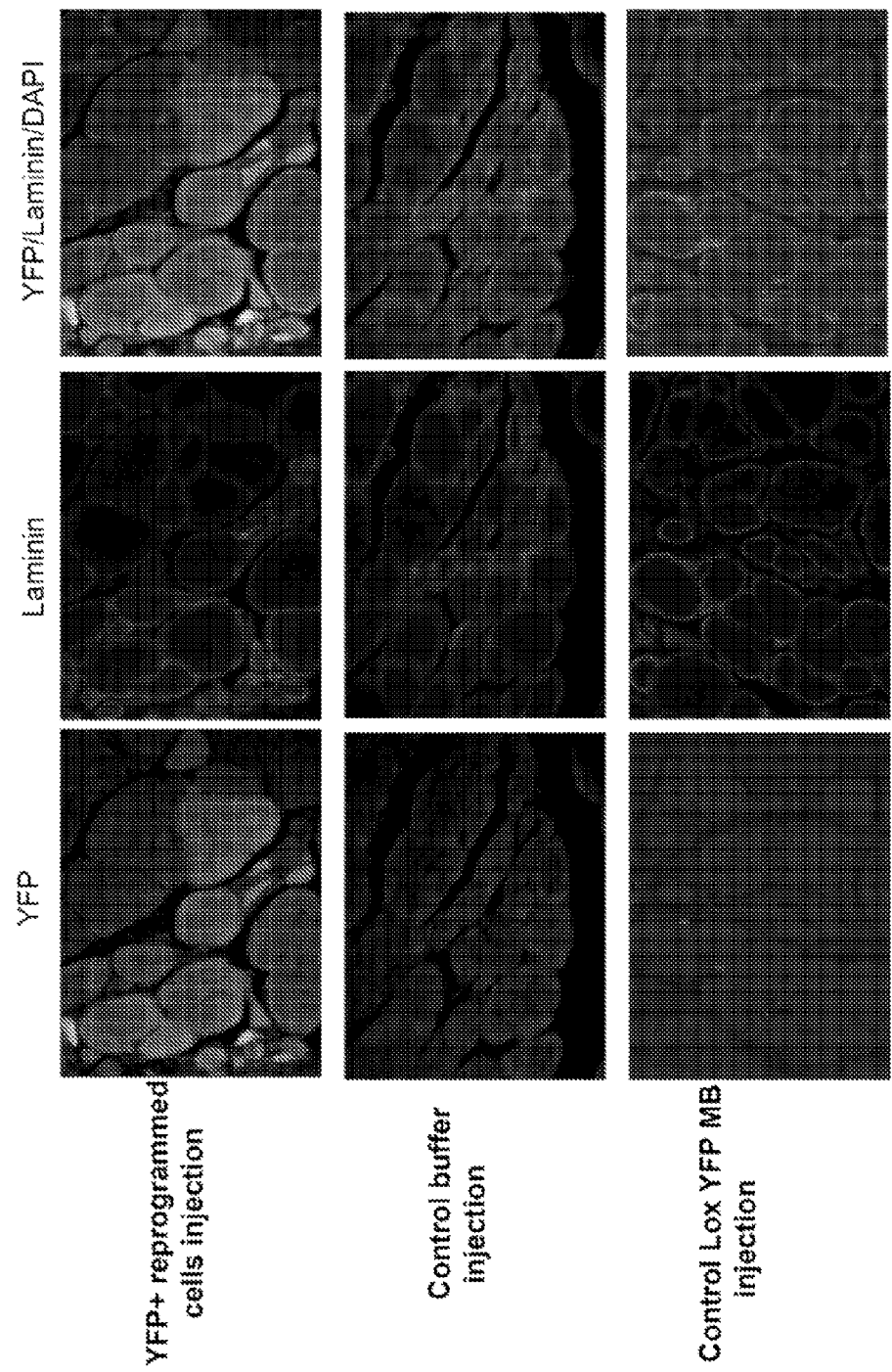
FIG. 5. Reprogrammed YFP$^+$ proliferative cells contribute to in vivo muscle regeneration. FACS sorted YFP$^+$ proliferating mononucleated cells were expanded in GM and injected in cardiotoxin injured Tibialis Anterior (TA) immuno-compromised NOD-SCID mice. 2-3 weeks later, TA muscles were dissected out, sectioned at 10 μm and co stained with YFP and laminin to visualize YFP$^+$ myofibers. Control buffer and Lox YFP myoblast injected TA muscle did not show any YFP$^+$ myofibers.

The ultimate test was to make sure that these reprogrammed cells could contribute to in vivo muscle regeneration under physiological conditions. The dividing de-differentiated YFP$^+$ cells were expanded in GM for ~1.5-2 weeks and injected into cardiotoxin injured Tibialis Anterior (TA) of immuno-deficient NOD-SCID mice. Injections of un-recombined Lox-YFP myoblasts and buffer medium served as negative controls. Two weeks of post injection, muscles were dissected out, sectioned and immunostained for YFP and laminin. YFP$^+$ reprogrammed cells readily fused with regenerating myofibers and contributed to muscle repair in vivo (FIG. 5). These results establish that post-mitotic myotubes can de-differentiate into functional, proliferating myogenic precursor cells that regenerate muscle tissue after an injury. Cultured muscle precursor cells that eagerly regenerate muscle in vivo were produced from terminally differentiated primary myotubes without an exogenous gene expression, making this method therapeutically feasible.

Example 5

Inhibitor Mix Treatment Modulates Gene Expression in Myotubes

Figure 6:
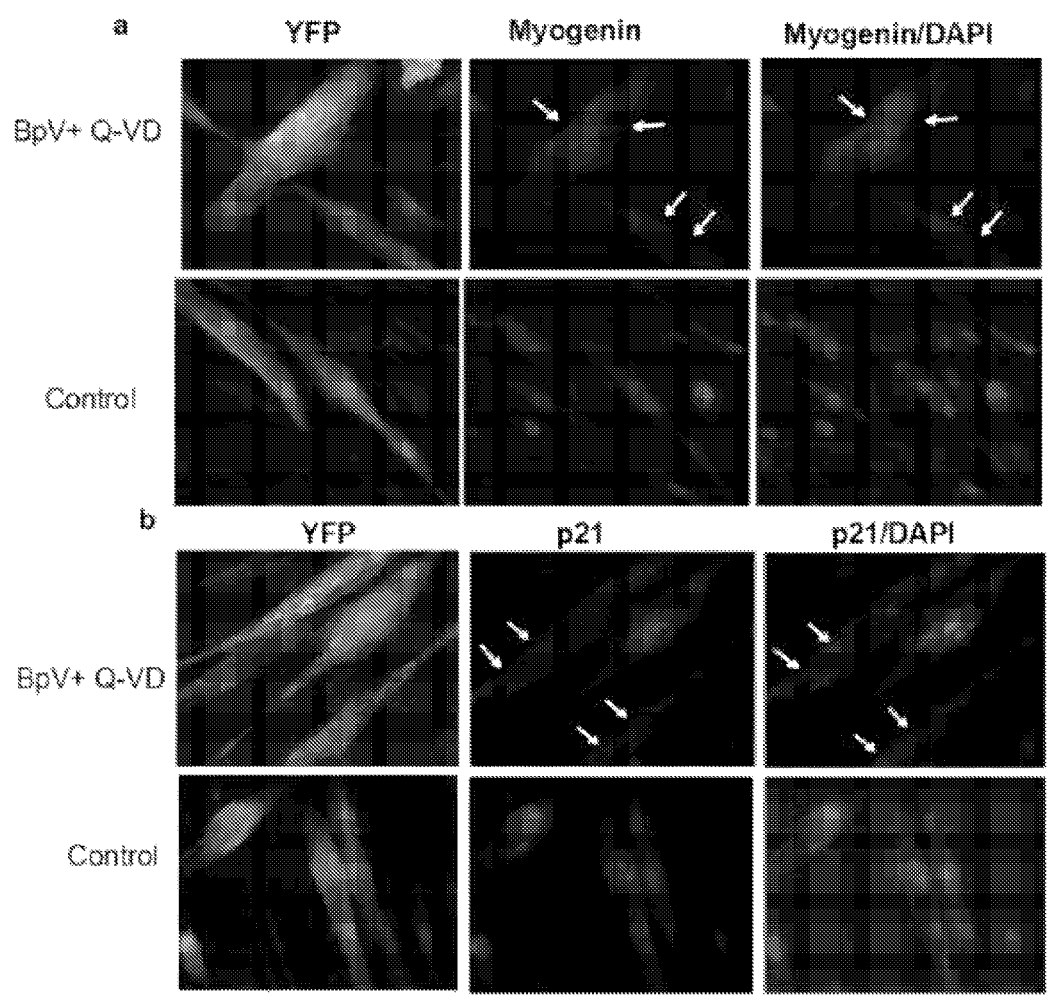
FIG. 6. Molecular analysis of reprogramming in genetically labeled myotubes. Inhibitor mix treatment down regulates muscle differentiation marker in Cre Lox-YFP myotubes.
Figure 6:
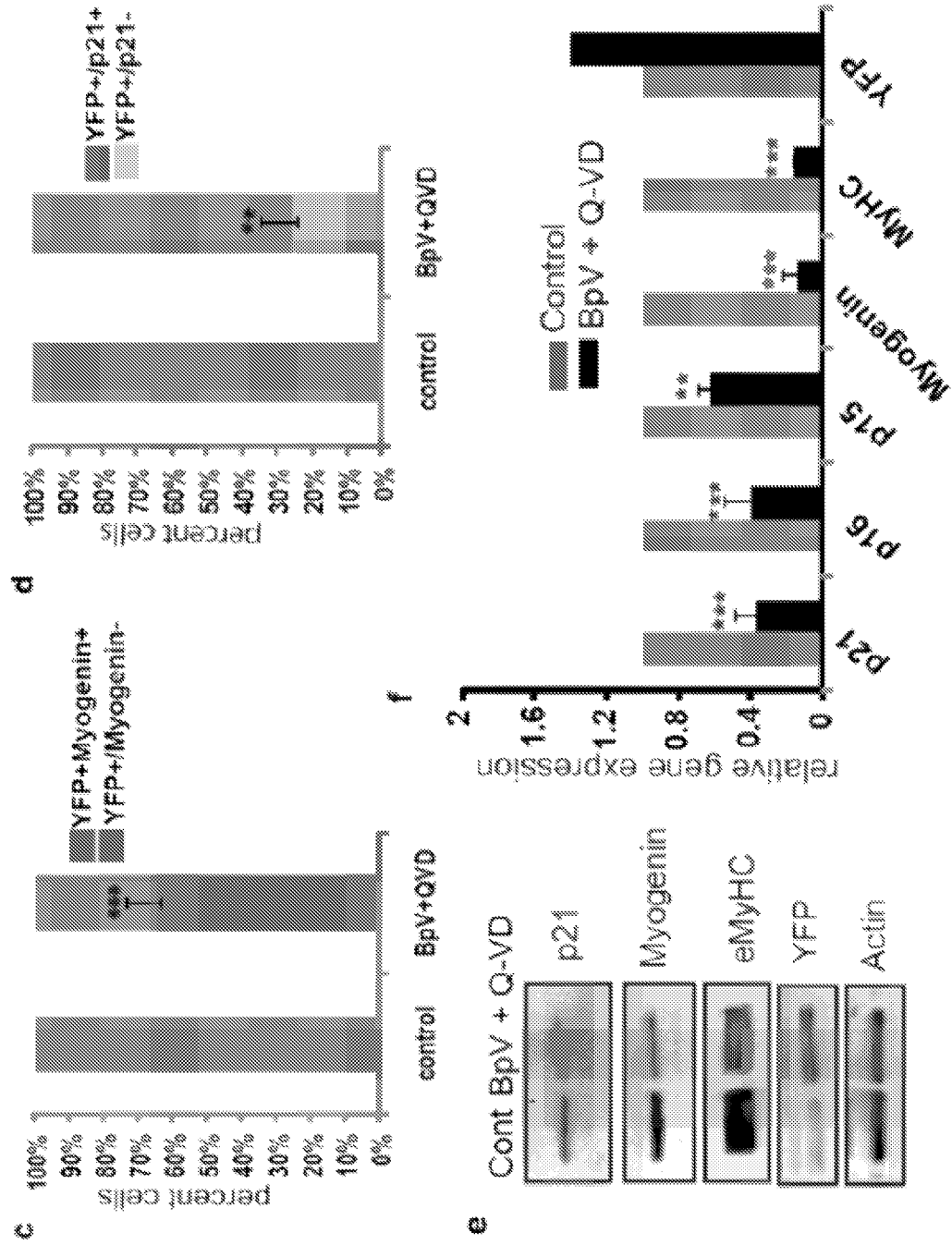

To address the mechanism by which inhibitor mix facilitated de-differentiation of YFP$^+$ myotubes, we analyzed early changes in expression of eMyHC (a terminal muscle differentiation marker), myogenin (a muscle marker expressed on onset of differentiation), p21, p15 and p16 (CDK inhibitors) in Ad-Cre-Lox YFP$^+$ myotubes treated with inhibitor mix for 48 hours (FIGS. 6A and 6B). By immunofluorescence, over 60% of the myonuclei in YFP$^+$ myotubes down regulated myogenin as compared to untreated myotubes whereas the levels of p21, a negative regulator of mitosis that plays an important role in cell-cycle arrest (Bunz et al., Science 282, 1497-1501, 1998; Cayrol et al., Oncogene 16, 311-320, 1998) were found to be attenuated in approximately 25% of the myonuclei present in YFP$^+$ myotubes (FIGS. 6C and 6D). The down regulation of eMyHC, p21, p15, p16 and myogenin in Ad-Cre-Lox-YFP$^+$ myotubes treated with inhibitor mix was also confirmed by western blotting experiments and qRT-PCR analysis (FIGS. 6E and 6F). These results demonstrate that the myogenic cell fate is reversed at the genetic level in multi-nucleated myotubes, before they split into single dividing cells. We also observed that inhibitor treatment increased the expression of YFP in Cre-Lox myotubes both at protein and RNA level. As shown earlier in FIG. 13A, Lox YFP myotubes do not express YFP spontaneously upon inhibitor mix treatment and in the absence of Cre recombinase. However when YFP locus is recombined, the broad range phosphatase inhibitor mix which is known to modulate numerous signaling pathways by acting at the transcriptional as well as post transcriptional levels might activate ROSA locus at the transcriptional level thereby increasing YFP expression.

Figure 7:
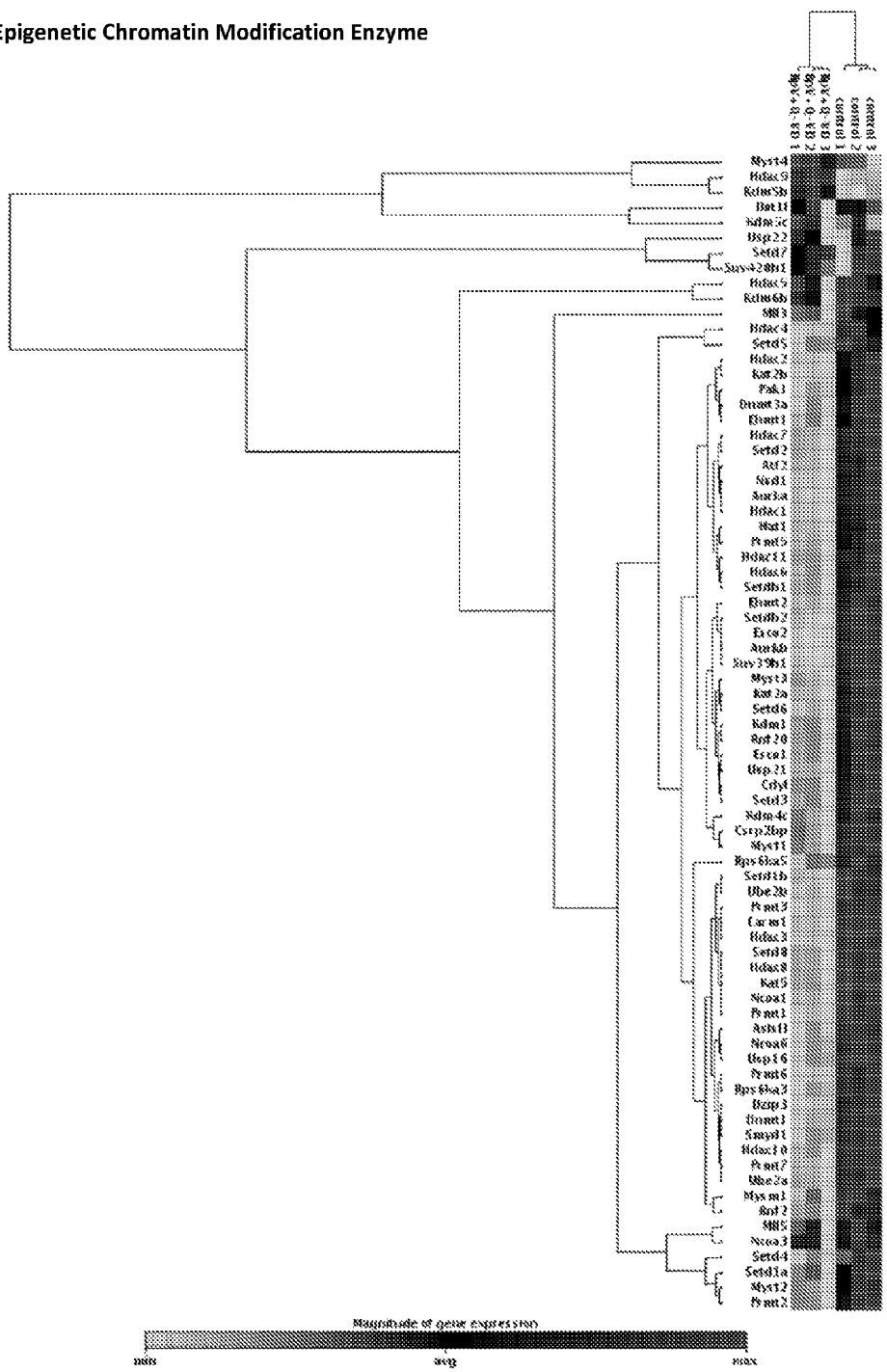
FIG. 7. Inhibitor mix treatment modulates chromatin remodeling factors and enzymes.
Figure 7:
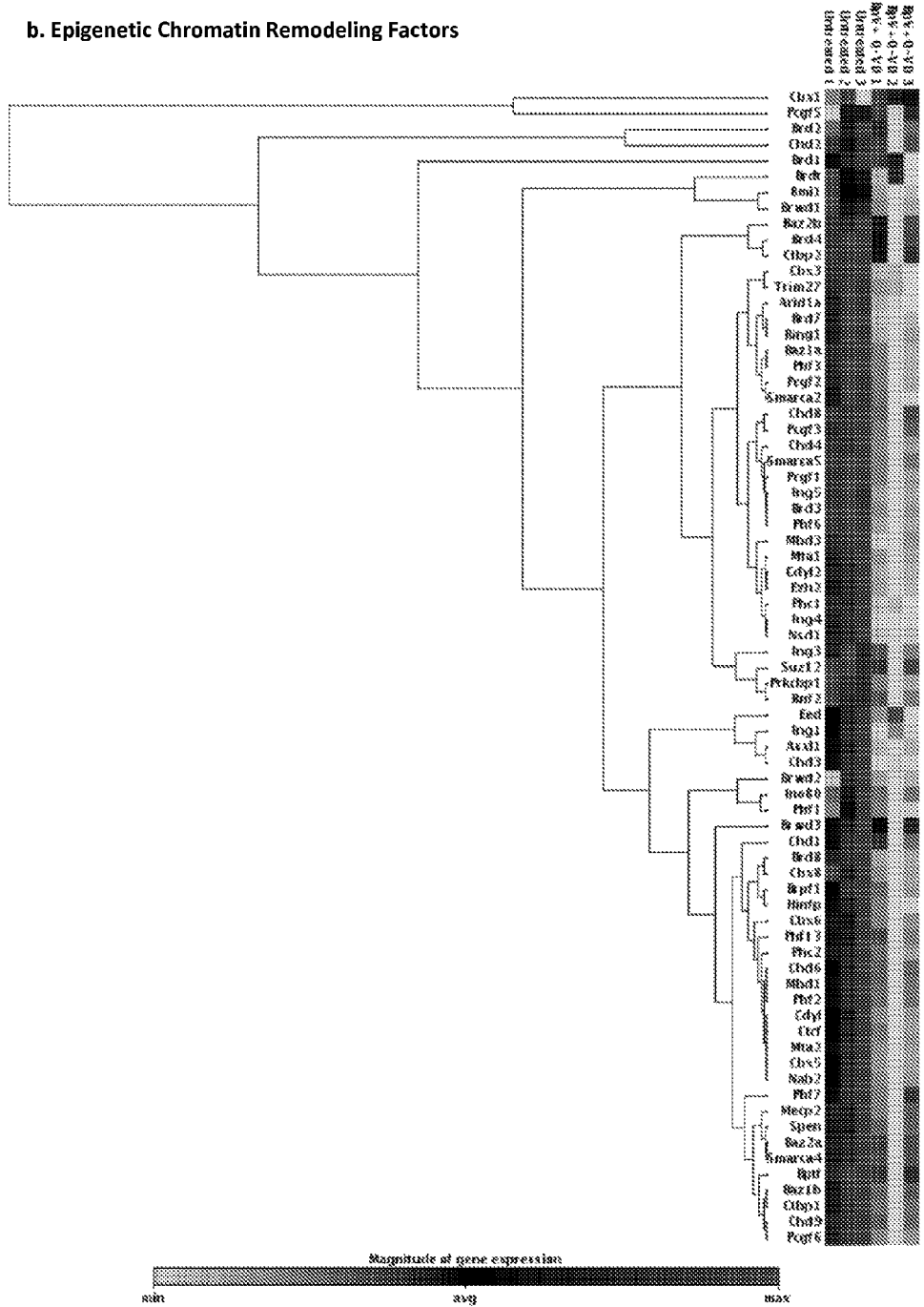
Figure 7:
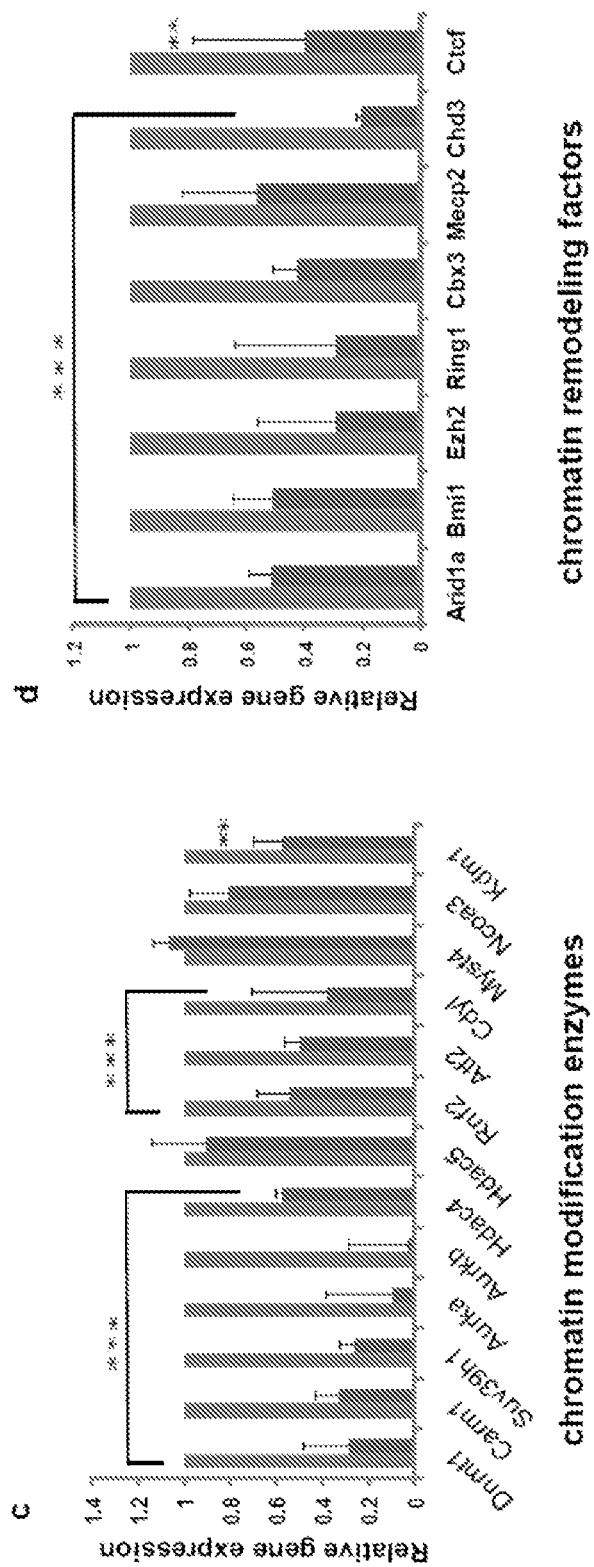

Studies have also shown that upon myotube differentiation, widespread chromatin remodeling occurs and genes necessary for differentiation are activated while those for proliferation are repressed (Forcales and Puri, Semin Cell Dev Biol 16, 596-611, 2005; Guasconi and Puri, Trends Cell Biol 19, 286-294, 2009; McKinsey et al., Curr Opin Cell Biol 14, 763-772, 2002; Palacios and Puri, J Cell Physiol 207, 1-11, 2006; Sartorelli and Caretti, Curr Opin Genet Dev 15, 528-535, 2005). Since a subset of labeled myotubes enter cell cycle and proliferate in GM, we reasoned that inhibitor mix have a global effect and perturbation of signaling pathways would in turn affect chromatin remodeling thereby facilitating reprogramming of myotubes to their progenitor cells. To analyze these changes during inhibitor mix treatment, PCR arrays for chromatin enzymes and chromatin remodeling factors was performed on untreated and inhibitor mix treated Cre-Lox YFP myotube cultures (FIG. 7). As summarized in FIGS. 7C and 7D, Carm1, Suv39h1, SWI/SNF complex components which have been earlier shown to promote myogenic differentiation (Ait-Si-Ali et al., EMBO J. 23, 605-615, 2004; Chen S. L., et al., J Biol Chem 277, 4324-4333, 2002; de la Serna et al., Nat Genet. 27, 187-190, 2001) were down regulated upon inhibitor mix treatment along with other histone methyltransferases. FIGS. 8 and 9 show Supplementary Tables S1 and S2 that provide a complete list of chromatin factor and enzyme genes modulated by inhibitor mix treatment. These findings suggest that inhibitor mix down-regulates the chromatin factors and enzymes dedicated to the maintenance of differentiated state in primary myotubes, enabling them to respond to the growth factors present in serum and de-differentiate to YFP$^+$ proliferating progenitor cells.

The studies presented herein explored the small molecule pharmacological approach to de-differentiation and reprogramming that does not involve over-expression of exogenous genes, which is the currently searched for method in the field of cell reprogramming. The use of a broad pharmacological inhibitor of tyrosine phosphatases simultaneously with the inhibition of apoptosis was, in our hands, sufficient to induce actual reprogramming of terminally differentiated post-mitotic multinucleated skeletal muscle cells into their progenitors. The use of small molecule inhibitors for reprogramming studies has high translational significance. The apoptosis inhibitors used in our studies is reversible treatment, has short half life and is not present in cells when expanded in vitro for transplantation experiments. Hence the reprogrammed myogenic progenitor cells transplanted with the aim to alleviate myopathic conditions will not be resistant to apoptosis and consequentially will not pose risk of cancers. In this work the irreversible cell-fate lineage marking of myotubes was based on the fact that terminally differentiated skeletal muscle cells are normally produced by the fusion of myoblasts. Thus, Lox-YFP Rosa 26 nuclei and Cre containing nuclei at some point coexisted in a multinucleated cell in order to produce YFP$^+$ myotubes. The Cre-Lox myotubes labeling method efficiently distinguishes reserve cells from multinucleated myotubes. Our data shows that 4 day old cultures of YFP$^+$ primary myotubes express typical muscle differentiation markers such as myogenin, eMyHC, express high levels of CDK inhibitor p21 and do not incorporate BrdU which strongly suggests that these YFP marked cells are indeed terminally differentiated (FIG. 2A-D). The observation that dividing YFP$^+$ mononucleated myogenic progeny were obtained from YFP$^+$ myotubes unambiguously establishes the reprogramming step toward a less differentiated precursor cell. Importantly, such genetic labeling for the first time demonstrates de-differentiation of mature 4-day old multinucleated primary myotubes into proliferating fusion-competent myoblasts that expand in vitro and repair muscle in vivo.

The calculation of reprogramming efficiency from terminally differentiated myotubes to the muscle progenitor cells is complicated by the fact that heterogenous Cre and Lox YFP myoblasts form YFP$^+$ myotubes where varying number of both myonuclei co-exist in the same multinucleated myotube. Further, only Lox YFP myonuclei and not Ad-Cre MB nuclei co-existing in YFP$^+$ myotubes will give rise to YFP$^+$ mononucleated cells when labeled myotube de-differentiates. Moreover, the de-differentiation of myotubes that are produced by syngeneic fusion events was not accounted for in our YFP labeling method. Hence, we estimated efficiency by two different methods. By method 1 total number of YFP$^+$ mononucleated cells was divided by the total number of YFP$^+$ myotubes before inhibitor treatment. Based on this method, efficiency was estimated ~12-13% in the presence of inhibitor mix as compared to BpV alone which was around ~1.18% (FIG. 11D). By method 2, the total number of YFP$^+$ mononucleated cells was divided by an estimated number of Lox YFP myonuclei present in all labeled YFP$^+$ myotubes before inhibitor treatment. This method gave an estimate of ~5% in presence of inhibitor mix and ~0.4% in presence of BpV alone (FIG. 11D). For the above reasons, we feel these calculations give very conservative estimates of de-differentiation. No matter, the method of quantification, BpV alone gave poor reprogramming efficiency and apoptotic inhibitor was needed to augment the de-differentiation likely by facilitating the survival of those myotubes which undergo reprogramming in the presence of phosphatase inhibitor.

Recent reports have shown that cells expressing higher levels of anti proliferative genes and those involved in senescence are indeed difficult to reprogram (Li et al., Nature 460, 1136-1139, 2009; Utikal et al., Nature 460, 1145-1148, 2009). Since myotubes are post-mitotically arrested cells which express high levels of CDK inhibitors, these may have low reprogramming efficiency. Studies have indicated that experimental down regulation of CDK inhibitors in post-mitotic myotubes results in accumulation of DNA damage, hinders cell cycle reentry and cause DNA fragmentation and apoptosis (Pajalunga et al., PLoS ONE 5, e11559, 2010). It has been shown that dividing cells robustly repair DNA damage (Nouspikel and Hanawalt, DNA Repair (Amst) 1, 59-75, 2002) and since our de-differentiated cells are cultured in mitogen-high growth medium (following the BpV and apoptosis inhibitor treatments) and are actively dividing, any DNA damage accumulated in myotubes is likely to be repaired during the process of DNA replication. Notably, our results definitively demonstrate that reprogrammed myotubes give rise to functional muscle progenitor cells which form new muscle in vitro and in vivo, hence no irreversible DNA damage or mutations occurred to compromise the myogenic properties of the de-differentiated cells. Recent studies has also shown that inhibition of Rb and p16/p19 can induce cell cycle entry in post mitotic myocytes (Pajcini et al., Cell Stem Cell 7, 198-213, 2010). Our work conducted on 4 day old mature myotubes not only down regulated CDK inhibitors and muscle differentiation markers but also decreased gene expression of chromatin remodelers that maintain differentiated state. The role of chromatin organization in establishment and maintenance of cell fates has been well defined. It has also been shown to play a role in commitment of myoblast to terminally differentiated myotubes as different signaling pathways have been shown to modulate chromatin signaling in muscle progenitor cells upon differentiation (Caretti et al., Genes Dev 18, 2627-2638, 2004; de la Serna et al., Nat Genet. 27, 187-190, 2001; McKinsey et al., 2002; Palacios and Puri, J Cell Physiol 207, 1-11, 2006). Recent work has also demonstrated the stage specific role of Ezh2 in muscle regeneration where Ezh2 occupies the Pax7 regulatory sequences in differentiated state (Palacios et al., Cell Stem Cell 7, 455-469, 2010). This suggests that in spite of down regulation of Ezh2 upon differentiation as reported earlier (Caretti et al., Genes Dev 18, 2627-2638, 2004), a certain level of Ezh2 along with other polycomb members would be required to maintain muscle progenitor genes in repressed state. Our PCR arrays on Cre-Lox myotubes after inhibitor mix treatment demonstrate significant down regulation of Ezh2 and other polycomb members as compared to untreated myotubes suggesting the creation of sensitized background in myotubes that may force them to re-express muscle progenitor genes and enter cell cycle.

Since a generic tyrosine phosphatase and apoptosis inhibitor were used which is expected to modulate signaling in many biochemical pathways, the down-regulation of specific chromatin remodeling factors predisposed primary myotubes to respond to the mitogens of GM thereby changing their cell fate to that of proliferating myogenic precursor cells. Interestingly, while upon addition of inhibitor mix there were profound changes in the morphology of many myotubes, only a subset of these myotubes de-differentiated into proliferating mono-nucleated precursor cells. Since there is temporal progression towards the degree of terminal differentiation in myotubes there might be a specific time window when myotubes would be more responsive to the treatment and capable of undergoing cell fate reversal. Future work can determine the exact role of chromatin remodeling factors in acquiring muscle progenitor cell fate from multinucleated post-mitotic differentiated state. As there is a temporal progression of gene expression upon myotube differentiation, it would be interesting to study in the future whether the inhibitor mix is sufficient to induce de-differentiation in mature myofibers formed in vivo or indeed other factors are required to yield regenerative cells.

Use of pharmacological inhibitors to modulate different signaling pathways without gene over expression is therapeutically relevant in coaxing differentiated cells to yield regenerative cells. Our data highlights the combinatorial use of tyrosine phosphatase and apoptosis inhibitors for primary myotube de-differentiation to yield myogenic proliferating cells which aided in muscle regeneration both in vitro and in vivo in SCID mice. The novel myotube labeling technique developed for this study served as a powerful tool to clearly show the origin of reprogrammed cells and to sort them away from reactivated reserve myoblasts. Importantly, small molecule inhibitors induced changes in myotubes at epigenetic level and facilitated them to enter proliferative state in mitogen rich medium. All together, the novel labeling technique employed along with the use of small molecule inhibitors advance the ongoing research in regenerative medicine and would enable unique clinical strategies for enhancing tissue regeneration.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:

contacting a differentiated cell in vitro with an effective amount of an agent that inhibits tyrosine phosphatases and an effective amount of an agent that inhibits apoptosis, wherein the agent that inhibits tyrosine phosphatases is potassium bisperoxo(1,10-phenanthroline)oxoyanadate (bpV(phen)) and the agent that inhibits apoptosis is N-(2-Quinolybyalyl-aspartyl-(2,6- difluorophenoxy)methyl ketone (Q-VD-oPh); and generating lineage-restricted progenitor cells from the differentiated cell, wherein the differentiated cell and the lineage-restricted progenitor cells have the same lineage, wherein the differentiated cell is a myocyte and the lineage-restricted progenitor cells are myogenic progenitor cells.

2. The method of claim 1, wherein the myocyte is a myocyte selected from the group consisting of a cardiomyoctyte, a smooth muscle myocyte, and a skeletal myocyte.

3. The method of claim 1, wherein the differentiated cell is from a subject with a disease.

4. The method of claim 1, wherein the method further comprises transferring the lineage-restricted progenitor cells to conditions that promote differentiation into differentiated cells of the same lineage as that of the differentiated cell contacted in the contacting step.

5. The method of claim 4, wherein the transferring comprises transferring the lineage-restricted progenitor cells into a subject.

6. The method of claim 5, wherein the subject is in need of tissue regeneration.

7. The method of claim 6, wherein the subject is suffering from loss of muscle function and/or loss of muscle mass, and wherein the differentiated cell is a myocyte and the lineage-restricted progenitor cells are myogenic progenitor cells.

8. A method comprising:

contacting a myotube in vitro with an effective amount of an agent that inhibits tyrosine phosphatases and an effective amount of an agent that inhibits apoptosis, wherein the agent that inhibits tyrosine phosphatases is potassium bisperoxo(1,10-phenanthroline)oxovanadate (bpV(phen)) and the agent that inhibits apoptosis is N-(2-Quinolyl)valyl-aspartyl-(2,6-difluorophenoxy) methyl ketone (Q-VD-oPh), wherein the myotube is a multinucleated skeletal muscle cell; and generating skeletal muscle progenitor cells from the myotube.

9. The method of claim 8, wherein the myotube is from a subject with a disease.

10. The method of claim 8, wherein the method further comprises transferring the skeletal muscle progenitor cells to conditions that promote differentiation into myotubes.

11. The method of claim 10, wherein the transferring comprises transferring the skeletal muscle progenitor cells into a subject.

12. The method of claim 11, wherein the subject is in need of skeletal muscle regeneration.

13. The method of claim 9, wherein the method further comprises transferring the skeletal muscle progenitor cells to conditions that promote differentiation into myotubes.

14. The method of claim 13, wherein the transferring comprises transferring the skeletal muscle progenitor cells into the subject.

15. The method of claim 14, wherein the subject is in need of skeletal muscle regeneration.

* * * * *